(12) United States Patent
Tsonton et al.

(10) Patent No.: US 7,862,517 B2
(45) Date of Patent: Jan. 4, 2011

(54) MRI BIOPSY DEVICE

(75) Inventors: Mark Tsonton, Loveland, OH (US); Timothy G. Dietz, Terrace Park, OH (US); John A. Hibner, Mason, OH (US); Jessica M. Pyzoha, Cincinnati, OH (US); Michael J. Andreyko, Cincinnati, OH (US); Keshava Datta, Mason, OH (US); Michael A. Murray, Bellevue, KY (US)

(73) Assignee: Devicor Medical Products, Inc., Cincinnati, OH (US)

( * ) Notice: Subject to any disclaimer, the term of this patent is extended or adjusted under 35 U.S.C. 154(b) by 397 days.

(21) Appl. No.: 11/834,034

(22) Filed: Aug. 6, 2007

(65) Prior Publication Data

US 2008/0015429 A1   Jan. 17, 2008

Related U.S. Application Data

(62) Division of application No. 11/103,718, filed on Apr. 12, 2005.

(60) Provisional application No. 60/573,510, filed on May 21, 2004.

(51) Int. Cl.
*A61B 10/00* (2006.01)
(52) U.S. Cl. ............... 600/567; 600/562; 600/564; 600/565; 600/566; 600/414
(58) Field of Classification Search ............ 600/562, 600/564, 567
See application file for complete search history.

(56) References Cited

U.S. PATENT DOCUMENTS

| | | | |
|---|---|---|---|
| 873,745 A | 12/1907 | Haynes | |
| 4,169,060 A | 9/1979 | Columbus | |
| 4,875,478 A | 10/1989 | Chen | |
| 5,057,085 A | 10/1991 | Kopans | |
| 5,211,165 A | 5/1993 | Dumoulin et al. | |

(Continued)

FOREIGN PATENT DOCUMENTS

DE    92 06 853.7    10/1992

(Continued)

OTHER PUBLICATIONS

U.S. Appl. No. 60/573,510, filed May 21, 2004, Hughes et al.

(Continued)

*Primary Examiner*—Long V Le
*Assistant Examiner*—Nicholas L Evoy
(74) *Attorney, Agent, or Firm*—Frost Brown Todd LLC

(57) ABSTRACT

A localization mechanism, or fixture, is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and in particular a sleeve, to a biopsy site of suspicious tissues or lesions. A depth stop enhances accurate insertion, and prevents over-insertion or inadvertent retraction of the sleeve. The sleeve receives a probe of the MRI-compatible biopsy instrument and may contain various features to enhance its imagability, to enhance vacuum and pressure assist therethrough, and marker deployment etc.

10 Claims, 30 Drawing Sheets

U.S. PATENT DOCUMENTS

| | | | |
|---|---|---|---|
| 5,307,808 | A | 5/1994 | Dumoulin et al. |
| 5,318,025 | A | 6/1994 | Dumoulin et al. |
| 5,437,277 | A | 8/1995 | Dumoulin et al. |
| 5,443,066 | A | 8/1995 | Dumoulin et al. |
| 5,445,150 | A | 8/1995 | Dumoulin et al. |
| 5,458,112 | A | 10/1995 | Weaver |
| 5,514,131 | A | 5/1996 | Edwards et al. |
| 5,526,822 | A | 6/1996 | Burbank et al. |
| 5,531,703 | A | 7/1996 | Skwarek et al. |
| 5,541,972 | A | 7/1996 | Anthony |
| 5,560,373 | A | 10/1996 | DeSantis |
| 5,611,352 | A | 3/1997 | Kobren et al. |
| 5,678,549 | A | 10/1997 | Heywang-Koebrunner et al. |
| 5,715,822 | A | 2/1998 | Watkins et al. |
| 5,775,333 | A | 7/1998 | Burbank et al. |
| 5,782,764 | A * | 7/1998 | Werne ..................... 600/411 |
| 5,800,389 | A | 9/1998 | Burney et al. |
| 5,827,305 | A | 10/1998 | Gordon |
| 5,830,219 | A | 11/1998 | Bird et al. |
| 5,855,554 | A | 1/1999 | Schneider et al. |
| 5,882,305 | A | 3/1999 | Dumoulin et al. |
| 5,913,863 | A | 6/1999 | Fischer et al. |
| 5,921,943 | A | 7/1999 | Kass |
| 5,954,670 | A | 9/1999 | Baker |
| 6,022,325 | A | 2/2000 | Siczek et al. |
| 6,036,632 | A | 3/2000 | Whitmore, III et al. |
| 6,048,321 | A | 4/2000 | McPherson et al. |
| 6,077,230 | A | 6/2000 | Gregoire et al. |
| 6,086,544 | A | 7/2000 | Hibner et al. |
| 6,142,955 | A | 11/2000 | Farascioni et al. |
| 6,165,137 | A | 12/2000 | Milliman et al. |
| 6,174,291 | B1 | 1/2001 | McMahon et al. |
| 6,203,524 | B1 | 3/2001 | Burney et al. |
| 6,261,241 | B1 | 7/2001 | Burbank et al. |
| 6,261,243 | B1 | 7/2001 | Burney et al. |
| 6,264,670 | B1 | 7/2001 | Chin |
| 6,270,506 | B1 | 8/2001 | Sittek et al. |
| 6,272,372 | B1 | 8/2001 | Fisher |
| 6,289,233 | B1 | 9/2001 | Dumoulin et al. |
| 6,321,613 | B1 | 11/2001 | Avidor |
| 6,416,510 | B1 | 7/2002 | Altman et al. |
| 6,428,498 | B2 | 8/2002 | Uflacker |
| 6,432,064 | B1 | 8/2002 | Hibner et al. |
| 6,447,477 | B2 | 9/2002 | Burney et al. |
| 6,471,700 | B1 | 10/2002 | Burbank et al. |
| 6,558,337 | B2 | 5/2003 | Dvorak et al. |
| 6,626,849 | B2 | 9/2003 | Huitema et al. |
| 6,638,235 | B2 | 10/2003 | Miller et al. |
| 6,659,338 | B1 | 12/2003 | Dittmann et al. |
| 6,675,037 | B1 | 1/2004 | Tsekos |
| 6,752,768 | B2 | 6/2004 | Burdorff et al. |
| 6,758,824 | B1 | 7/2004 | Miller et al. |
| 6,758,848 | B2 | 7/2004 | Burbank et al. |
| 6,770,063 | B2 | 8/2004 | Goldberg et al. |
| 6,846,320 | B2 | 1/2005 | Ashby et al. |
| 6,863,676 | B2 | 3/2005 | Lee et al. |
| 6,889,073 | B2 | 5/2005 | Lampman et al. |
| 6,921,943 | B2 | 7/2005 | Kenney et al. |
| 6,975,701 | B2 | 12/2005 | Galkin |
| 6,999,553 | B2 | 2/2006 | Livingston |
| 7,160,292 | B2 | 1/2007 | Moorman et al. |
| 7,171,256 | B1 | 1/2007 | Graessle et al. |
| 7,276,032 | B2 | 10/2007 | Hibner |
| 7,347,829 | B2 | 3/2008 | Mark et al. |
| 7,351,228 | B2 | 4/2008 | Keane et al. |
| 2001/0049502 | A1 | 12/2001 | Chen |
| 2003/0004529 | A1 | 1/2003 | Tsonton et al. |
| 2003/0023239 | A1 | 1/2003 | Burbank et al. |
| 2003/0109802 | A1 | 6/2003 | Laeseke et al. |
| 2003/0109803 | A1 | 6/2003 | Huitema et al. |
| 2003/0199753 | A1 | 10/2003 | Hibner et al. |
| 2003/0199754 | A1 | 10/2003 | Hibner et al. |
| 2003/0199785 | A1 | 10/2003 | Hibner et al. |
| 2004/0006347 | A1 | 1/2004 | Sproul |
| 2004/0077938 | A1 | 4/2004 | Mark et al. |
| 2004/0077972 | A1 | 4/2004 | Tsonton et al. |
| 2004/0210161 | A1 | 10/2004 | Burdorff et al. |
| 2004/0230157 | A1 | 11/2004 | Perry et al. |
| 2008/0161720 | A1 | 7/2008 | Nicoson et al. |
| 2008/0200834 | A1 | 8/2008 | Mark et al. |

FOREIGN PATENT DOCUMENTS

| | | |
|---|---|---|
| DE | 42 16 694 | 12/1992 |
| EP | 0 995 400 | 4/2000 |
| EP | 1 410 764 | 4/2004 |
| EP | 1 598 006 | 11/2005 |
| EP | 1 598 015 | 11/2005 |
| FR | 2 332 743 | 6/1977 |
| WO | WO 93/17620 | 9/1993 |
| WO | WO 96/14023 | 5/1996 |
| WO | WO 98/22022 | 5/1998 |
| WO | WO 02/13709 | 2/2002 |
| WO | WO 03/026509 | 4/2003 |
| WO | WO 2005/017775 | 2/2005 |

OTHER PUBLICATIONS

U.S. Appl. No. 11/025,556, filed Dec. 29, 2004, Hibner et al.
U.S. Appl. No. 11/076,612, filed Mar. 10, 2005, Hughes et al.
U.S. Appl. No. 11/103,718, filed Apr. 12, 2005, Tsonton et al.
U.S. Appl. No. 11/103,959, filed Apr. 12, 2005, Hughes et al.
European Search Report dated Jan. 5, 2004 for EPO Application No. 03252518.0.
European Search Report dated Sep. 23, 2005 for Application No. 05253171.
European Search Report dated Sep. 20, 2005 for Application No. PCT/US2005/017775.
European Search Report dated May 21, 2007 for Application No. 07250438.4, pp. 1-5.
European Search Report dated Sep. 25, 2007 for Application No. 07252089.3.
Encor TM MRI Specifications and Breast Biopsy System, SenoRx, 2005, pp. 1-2.
Noras Medizintechnik, Operator Manual, Model MR-B1 160, Revision 3, pp. 1-11 Nov. 20, 2000 as per p. 3 of doc.
Preliminary Patentability Report dated Nov. 21, 2006 for Application No. PCT/US2005/017775.
Heywant-Köbrunner et al. "MR-guided percutaneous excisional and incisional biopsy of breast lesions," Eur. Radiol., vol. 9 (1999) pp. 1656-1665.
Savitz, M.H., "CT-Guided Needle Procedures for Brain Lesions: 20 Years' Experience," The Mount Sinai Journal of Medicine, vol. 67(4) (Sep. 2000) pp. 318-321.
Savitz, M.H., "Free-hand CT-guided Needle for Biopsy and Drainage of Intracerebral Lesions. Ten Years Experience," Int. Surg., vol. 77 (1992) pp. 211-215.
Perlot, C. et al., "Multicenter study for the evaluation of a dedicated biopsy device for MR-guided vacuum biopsy of the breast," Eur. Radiol., vol. 12 (2002) pp. 1463-1470.
Viehweg, P. et al., "MR-guided interventional breast procedures considering vacuum biopsy in particular," Eur. J. of Radiol., vol. 42 (2002) pp. 32-39.
Daniel, B.L. et al., "An MRI-Compatible Semiautomated Vacuum-Assisted Breast Biopsy System: Initial Feasibility Study," J. of Magnetic Resonance Imaging, vol. 21 (2005) pp. 637-644.
Kuhl, C.K. et al., "Interventional Breast MR Imaging: Clinical Use of a Stereotactic Localization and Biopsy Device," Radiology, vol. 204 (1997) pp. 667-675.
Written Opinion dated Sep. 29, 2005 for Application No. PCT/US2005/017775.

* cited by examiner

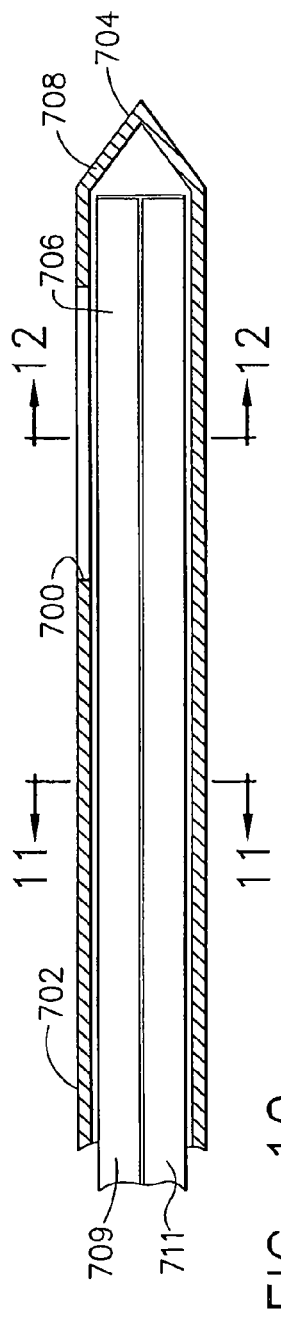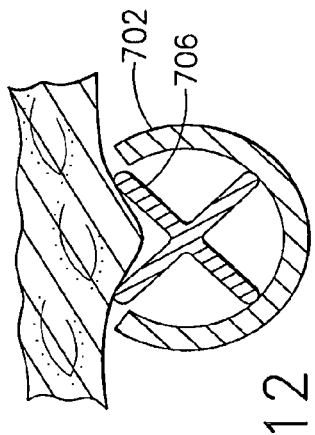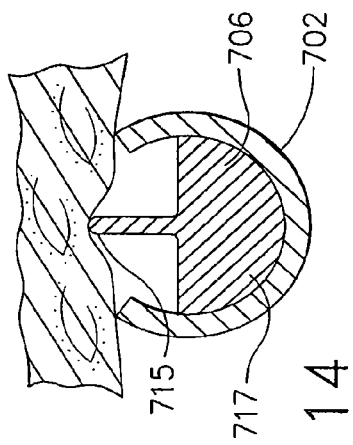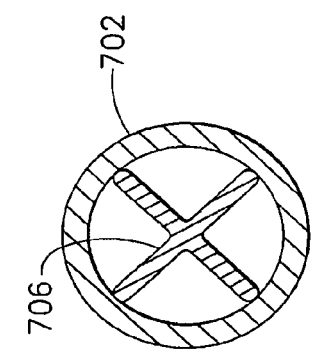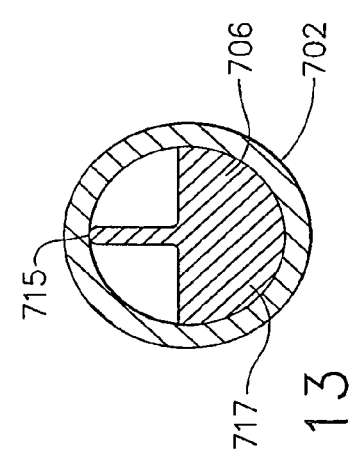

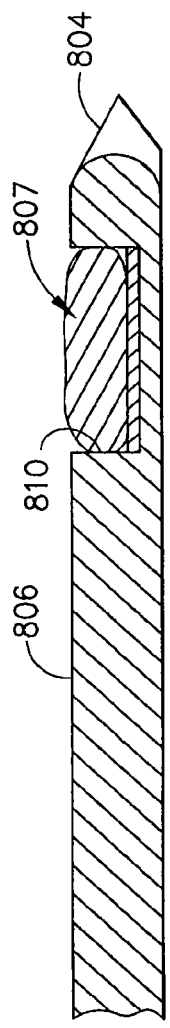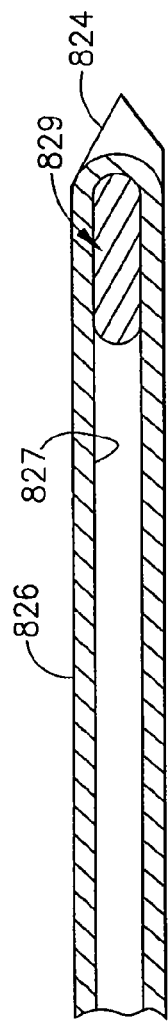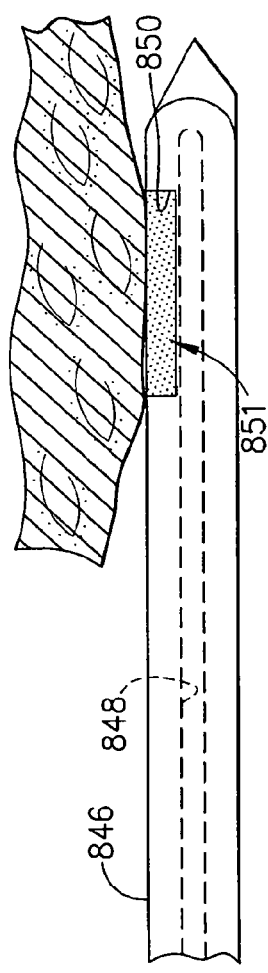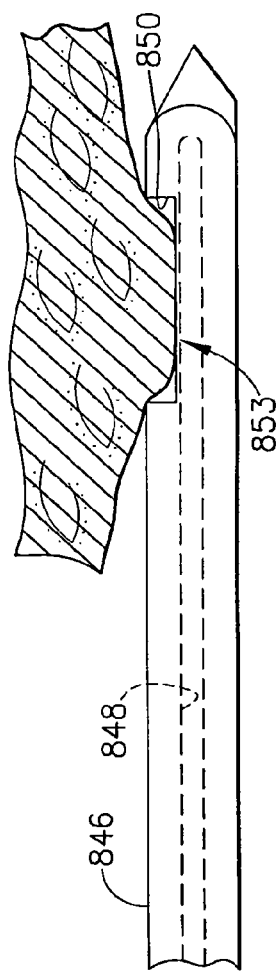

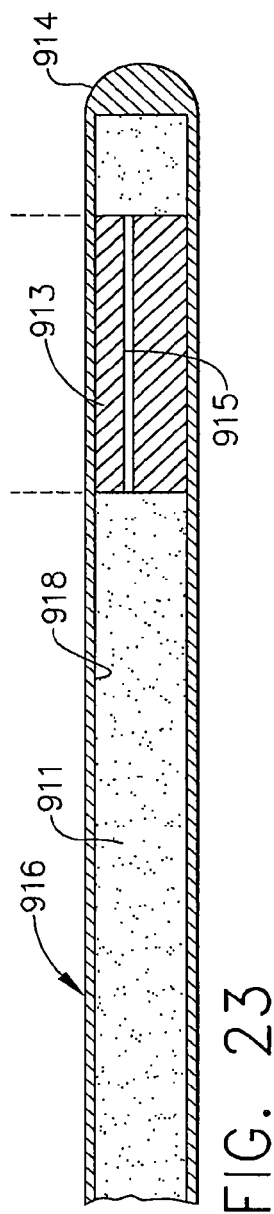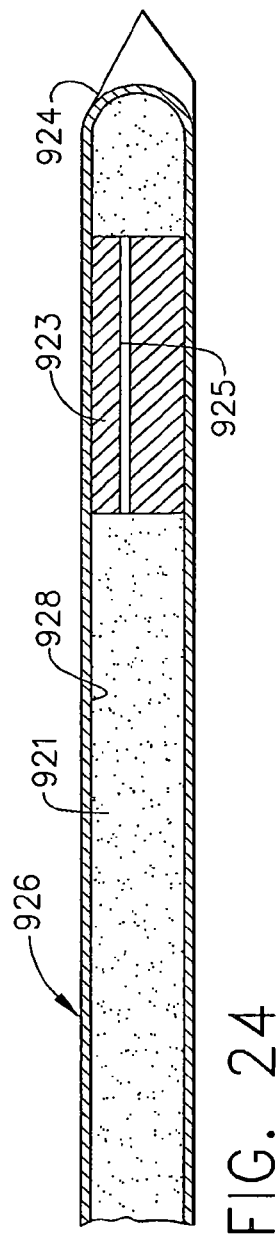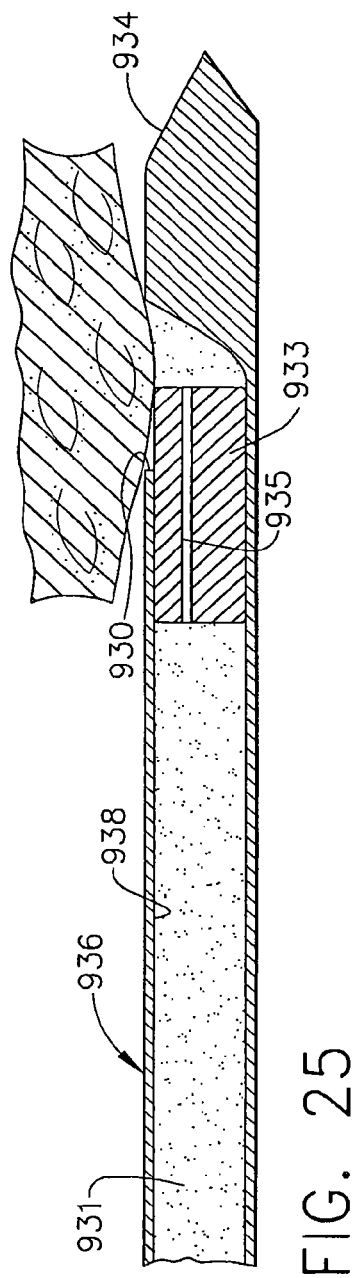

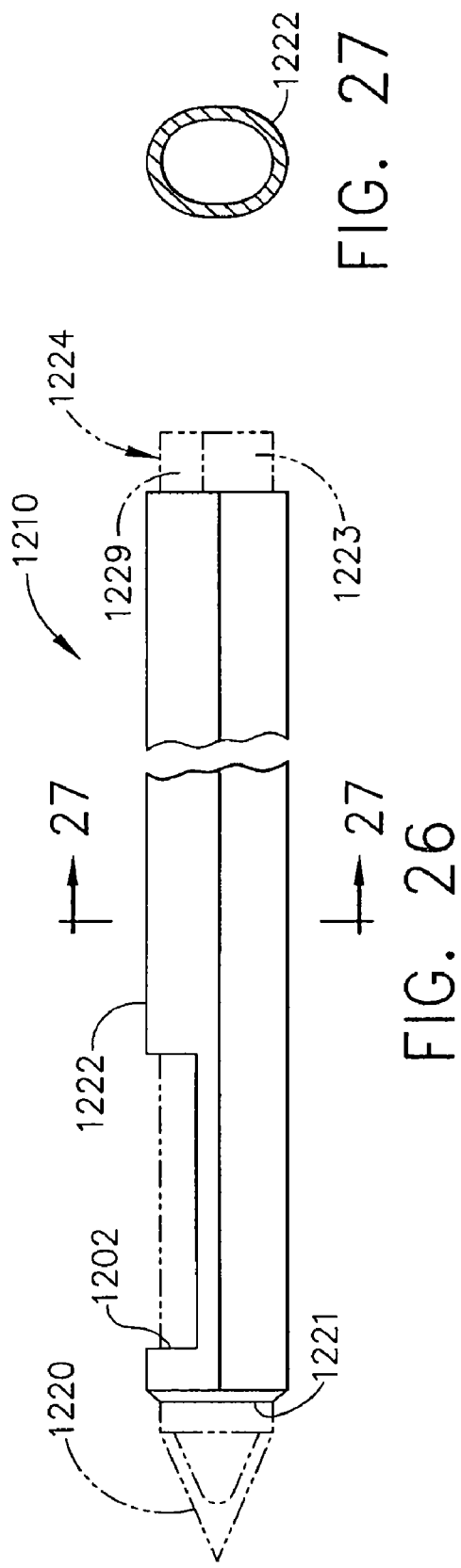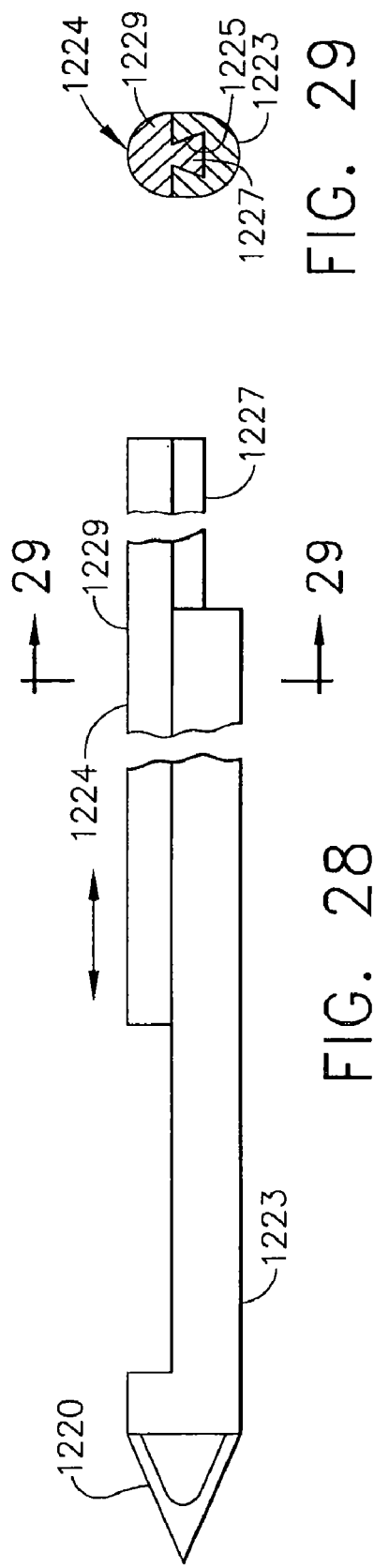

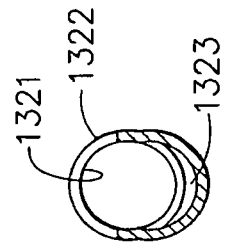
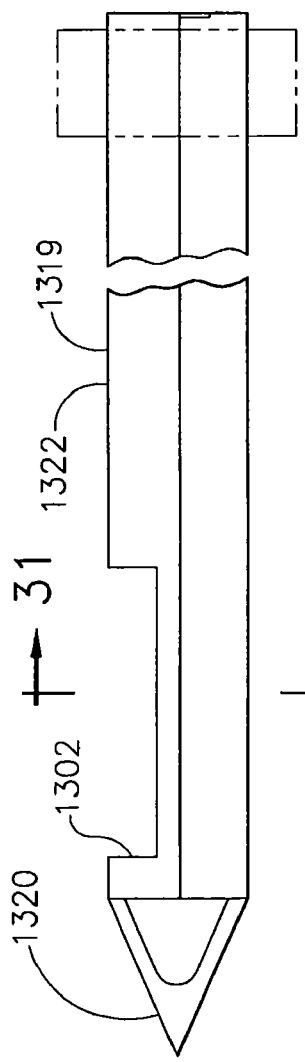
FIG. 31
FIG. 30
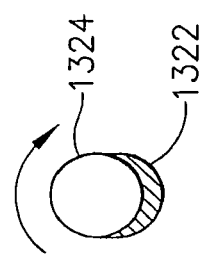
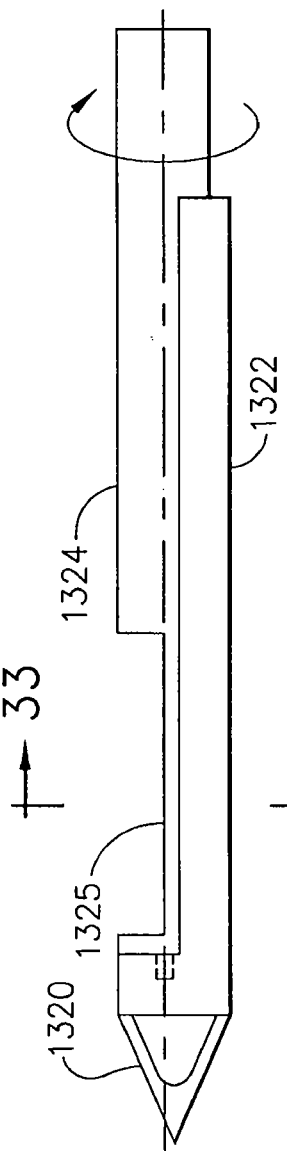
FIG. 33
FIG. 32

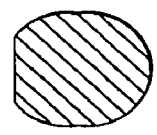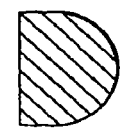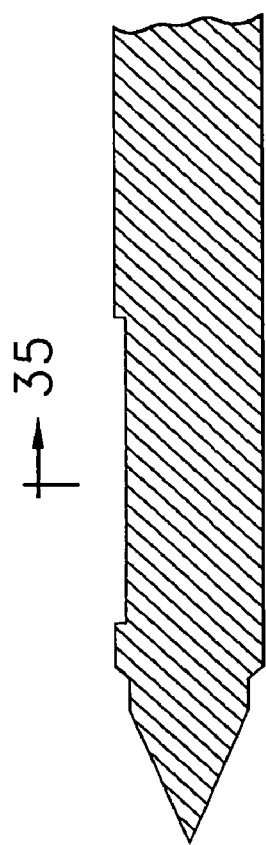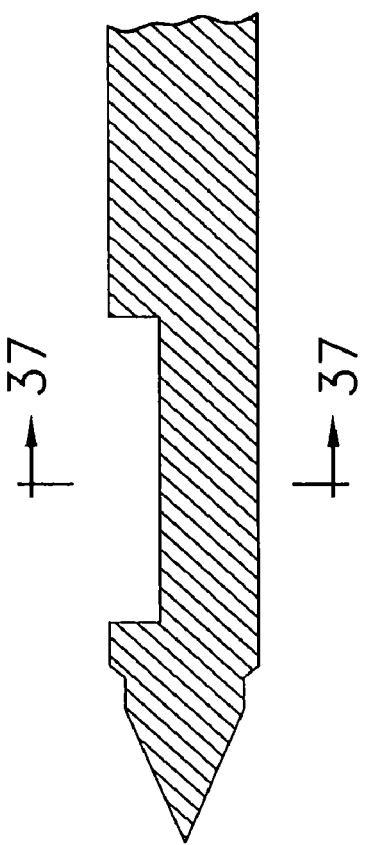

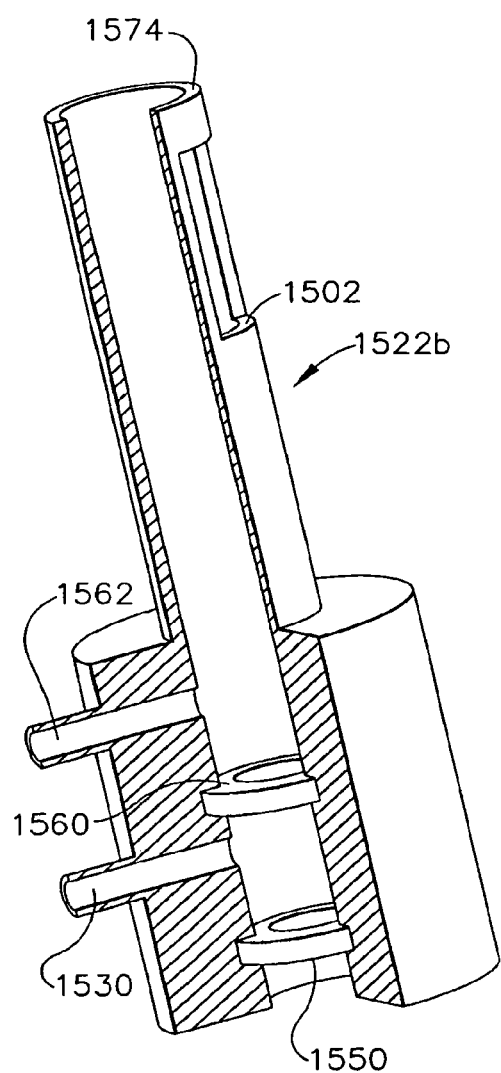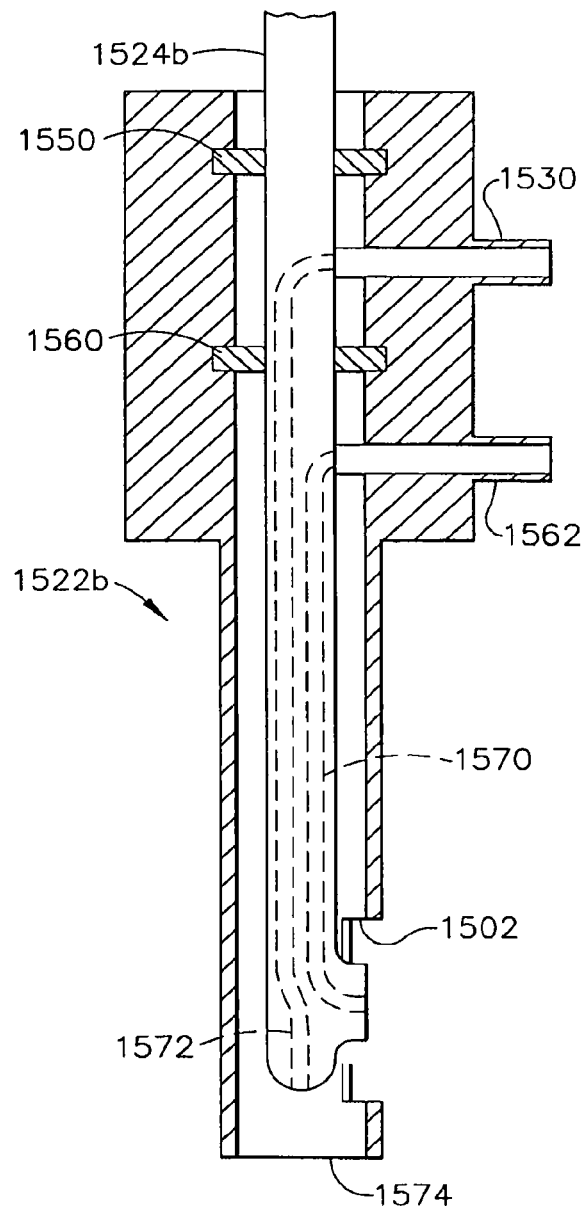
FIG. 45
FIG. 46

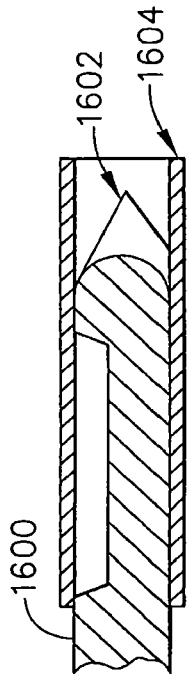
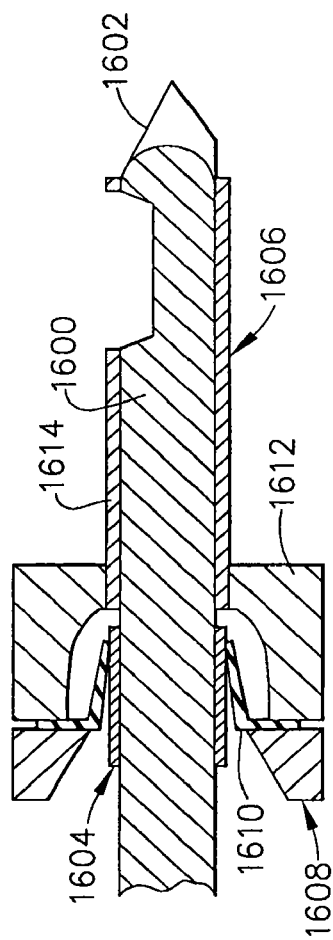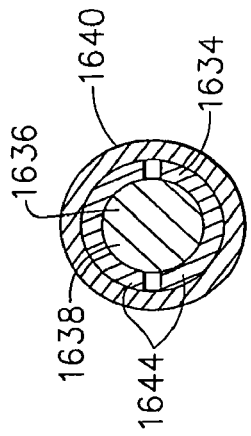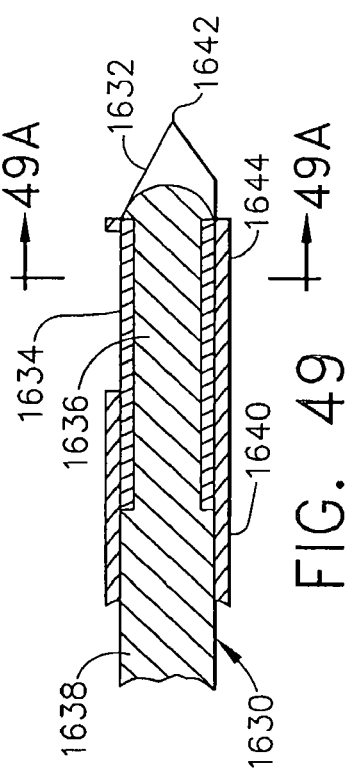

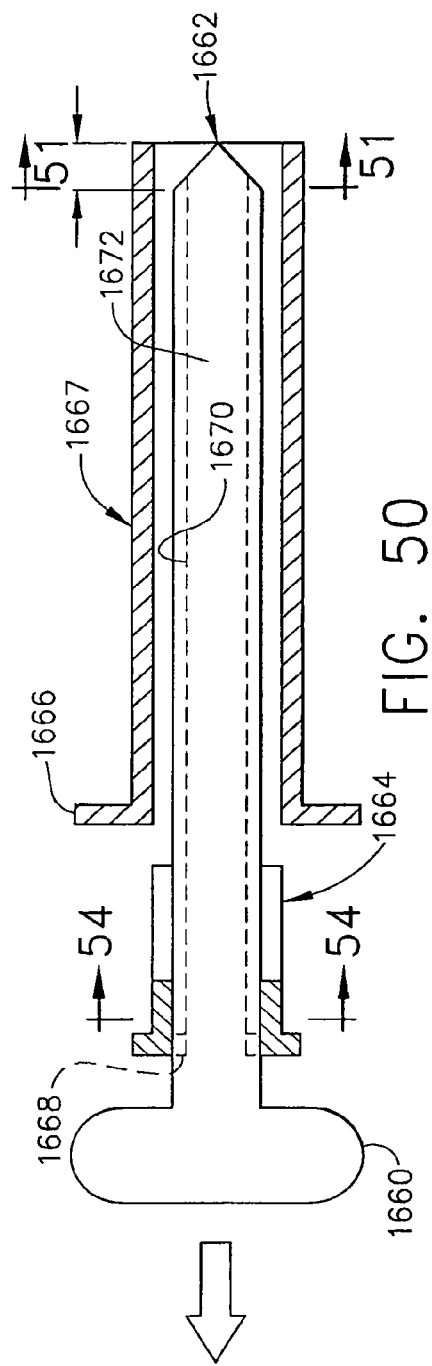
FIG. 50
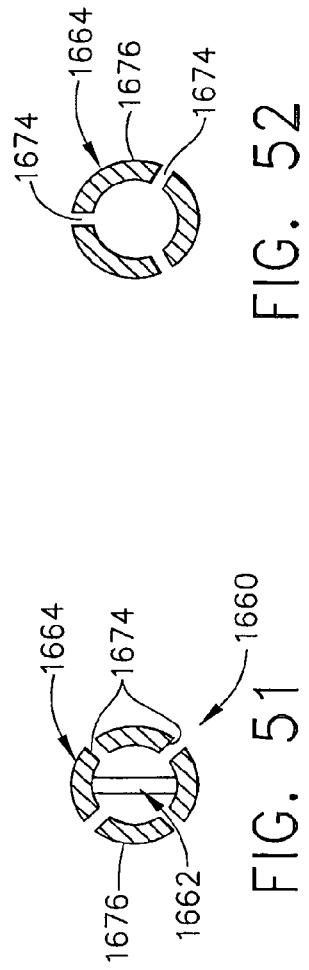
FIG. 51
FIG. 52
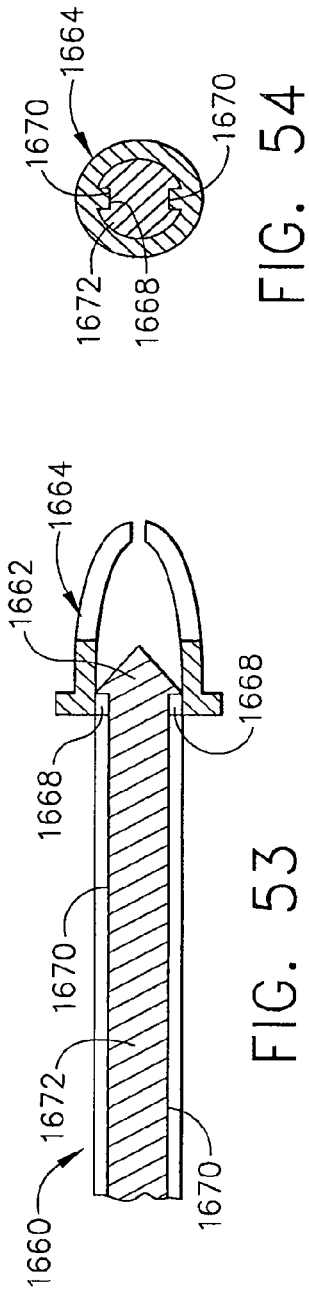
FIG. 53
FIG. 54

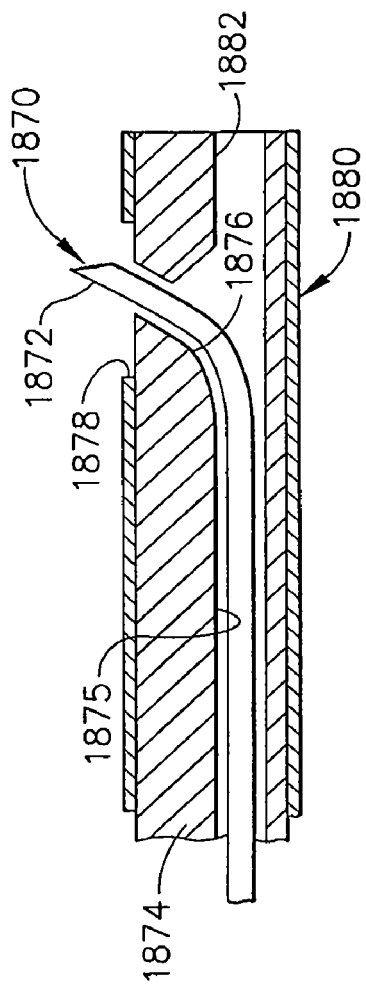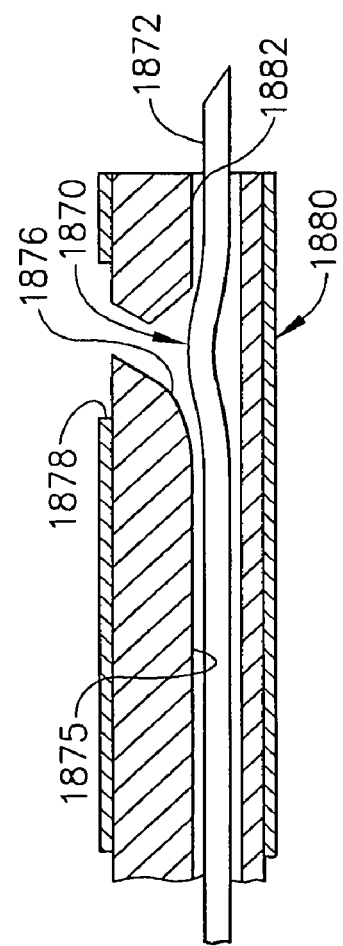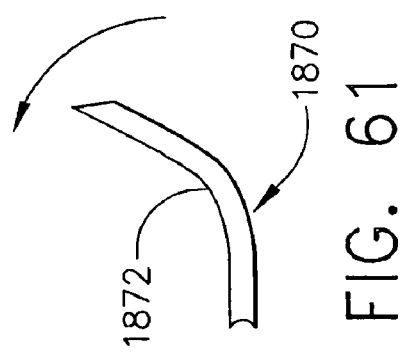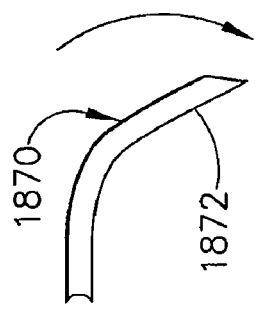

ROUND

OVAL

SQUARE/
RECTANGLE

COMPLEX

NO
COMPRESSION

COMPRESS

AFTER HEAT
REMOVE
COMPRESSION

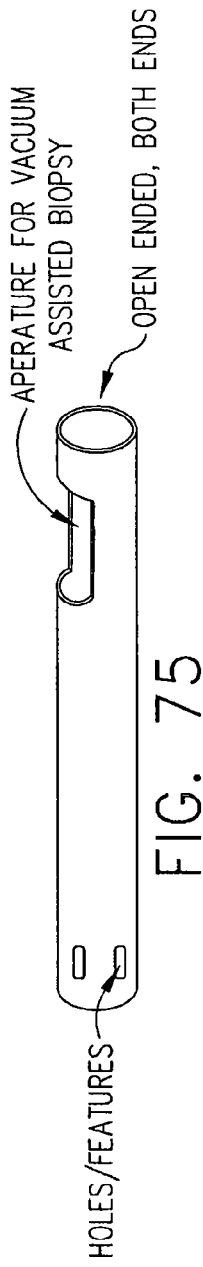
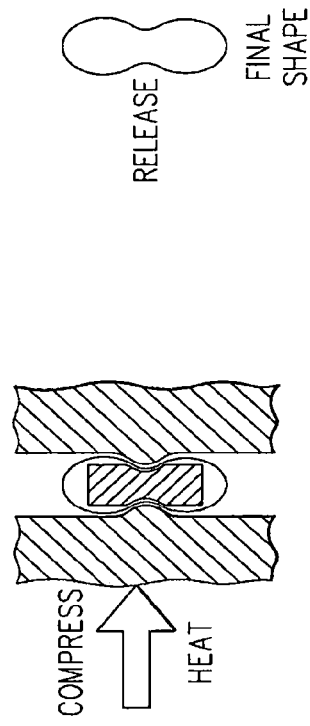
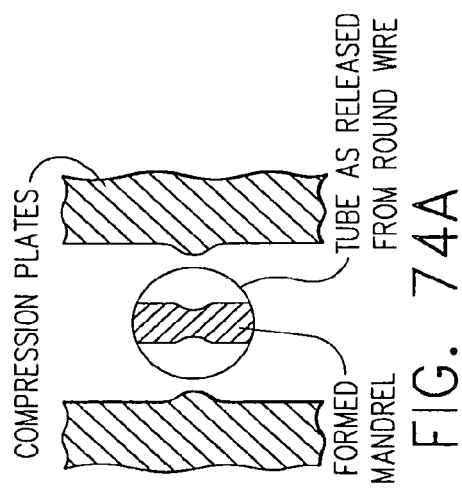
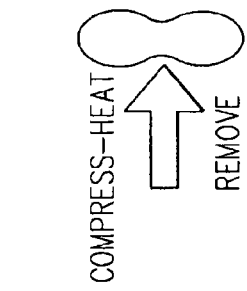
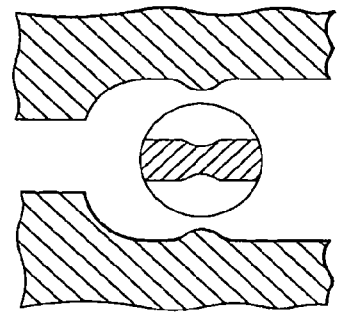

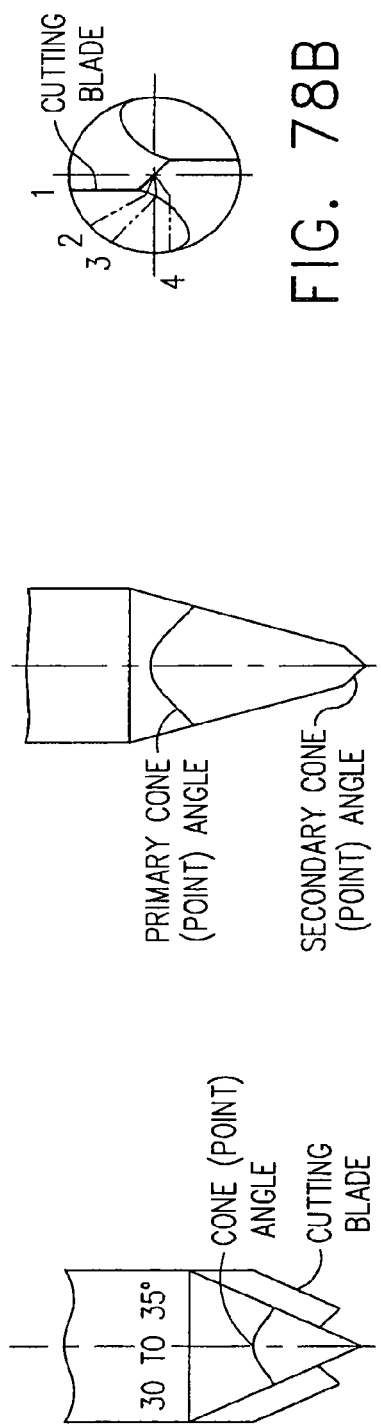
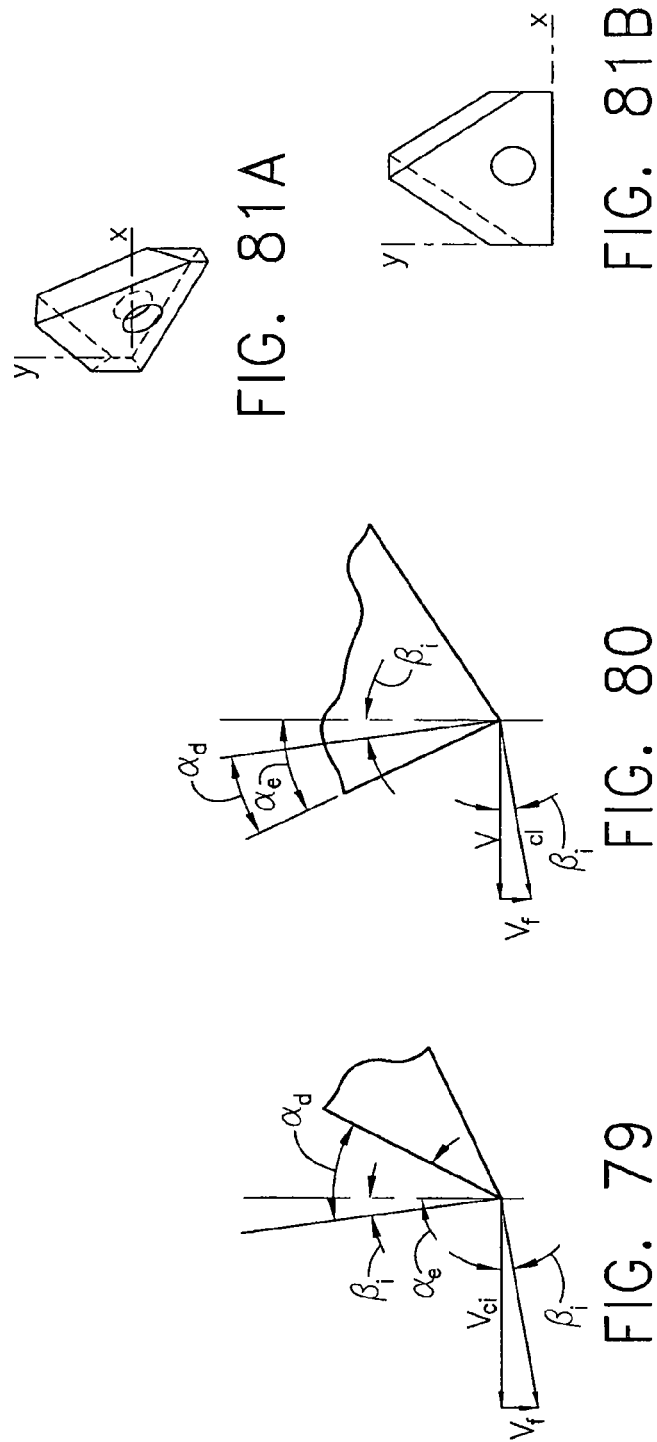
FIG. 78B
FIG. 78A
FIG. 77
FIG. 81A
FIG. 81B
FIG. 80
FIG. 79

MRI BIOPSY DEVICE

CROSS REFERENCE TO RELATED APPLICATIONS

This Divisional Application Claims priority to, and incorporates by reference, U.S. Ser. No. 11/103,718 filed Apr. 12, 2005.

The present application claims the benefit of U.S. provisional patent application entitled "MRI BIOPSY DEVICE" to Hughes et al., Ser. No. 60/573,510, filed on 21 May 2004, the disclosure of which is hereby incorporated by reference in its entirety.

FIELD OF THE INVENTION

The present invention relates, in general, to a method of imaging assisted tissue sampling and, more particularly, to an improved method for positioning a biopsy probe with respect to a magnetic resonance imaging (MRI) breast coil for acquiring subcutaneous biopsies and for removing lesions.

BACKGROUND OF THE INVENTION

Recently, core biopsy devices have been combined with imaging technology to better target a lesion in breast tissues. One such commercially available product is marketed under the trademark name MAMMOTOME™, by Ethicon Endo-Surgery, Inc. An embodiment of such a device is described in U.S. Pat. No. 5,526,822 issued to Burbank, et al., on Jun. 18, 1996, and is hereby incorporated herein by reference. Its handle receives mechanical and electrical power as well as vacuum assist from a remotely positioned control module that is spaced away from the high magnetic field of a Magnetic Resonance Imaging (MRI) machine.

As seen from that reference, the instrument is a type of image-guided, percutaneous coring, breast biopsy instrument. It is vacuum-assisted, and some of the steps for retrieving the tissue samples have been automated. The physician uses this device to capture "actively" (using the vacuum) the tissue prior to severing it from the body. This allows the sampling of tissues of varying hardness. In addition, a side opening aperture is used, avoiding having to thrust into a lesion, which may tend to push the mass away, causing a track metastasis, or causing a hematoma that, with residual contrast agent circulating therein, may mimic enhancement in a suspicious lesion. The side aperture may be rotated about a longitudinal axis of the probe, thereby allowing multiple tissue samples without having to otherwise reposition the probe. These features allow for substantial sampling of large lesions and complete removal of small ones.

In MRI, the presence of both the magnetic and RF fields used in the imaging process place several constraints on each instrument to be positioned or manipulated near or in the imaging region of the MRI system. The MRI system imposes a strong constant magnetic field (e.g, 1 Tesla) to align electrons of the atoms of the body. Then a magnetic gradient is applied to disturb these aligned electrons. As the electrons return to alignment, a weak RF signal is emitted that must be detected and interpreted. Compatibility with such an environment requires that the instrument must be essentially non-ferromagnetic, so that it is not attracted by the magnetic field and thus posing, which would pose a safety problem. This consideration applies to any object that is used near (or that is inserted into or implanted within) the patient being imaged, because the magnetic field subjects such an object or implants, if ferro-magnetic, to undesirable forces and torques. In addition, an electrical instrument should be tolerant of the static and pulsed magnetic and RF fields in order to be operable in the presence of these fields. Further, an implant or instrument should not be unduly subject to induced heating due to eddy current from the applied RF field. Finally, the instrument should not create excessive imaging artifacts that obscure or distort the image of the target.

To address these constraints, MRI compatible biopsy instruments are generally assembled from non-ferrous materials; however, other materials that are MRI imagable. are sometimes used. In some instances, imagability relies upon the lack of an MRI RF return image to contrast with the image returned by adjacent tissue. Also, ferromagnetic particles or liquid lumens for holding aqueous paramagnetic ions are sometimes incorporated.

While these generally-known MRI biopsy devices provide MRI compatibility and a degree of imagability, further improvements would be desirable. More particularly, a significant need exists for an MRI compatible biopsy device that may assist in penetrating tissue, that enhances locating a sampling aperture in an MRI compatible penetrating portion, even in an MRI scan slice that obliquely passes through the probe, and that facilitates other therapeutic steps through the penetrating portion.

BRIEF SUMMARY OF THE INVENTION

The invention overcomes the above-noted and other deficiencies of the prior art by providing a sleeve and obturator combination that facilitate minimally invasive procedures guided by diagnostic imaging by providing improvements in confirmation of sleeve placement and hands free continued access through the sleeve for a myriad of diagnostic and therapeutic procedures.

In one aspect of the invention, an apparatus performs a minimally invasive medical procedure into human breast tissue through a cannula formed of a magnetic resonance imaging (MRI) compatible material and including an open proximal end and a more distal opening. An obturator has a hollow shaft also formed of MRI compatible material and sized for insertion into the cannula. The obturator has a structure proximate to the more distal opening of the cannula when thus inserted into the cannula that controls prolapsing of tissue therein. Confirmation of placement of the cannula is accentuated by an MRI imagable portion of the obturator proximate to the more distal opening of the cannula. A lumen formed in the obturator communicates between a proximal portion external to the human breast tissue and the more distal opening of the cannula. Thereby, the obturator provides flexibility in performing steps such as transferal of pneumatic pressure for insufflation and marker deployment, removal of excess fluid, insertion of pharmacological or anesthetic substances or other procedures. In situations in which MRI imaging allows real-time confirmation of placement, the sleeve and obturator provides a means of accurately placing the cannula while mitigating tissue trauma as well as enabling treatments through the combination.

In another aspect of the invention, an apparatus is included for use with a biopsy device in a medical procedure wherein a patient has a body portion localized within a localization fixture having a guidance portion. The apparatus includes a sleeve having a hub supported and guided by the guidance portion of the localization fixture. The sleeve has a cannula that is inserted into the tissue with the assistance of an obturator, one of the two having a piercing tip. The cannula is sized to receive the elongate probe from a proximal direction through the sleeve hub. Thereby, clinical flexibility is achieved by being able to perform a number of therapeutic and diagnostic procedures hands free through the sleeve even within the close confines of certain diagnostic imaging modalities such as magnetic resonance imaging.

The present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 is a right side diagrammatic view in elevation taken in longitudinal cross section of a sleeve with an asymmetric piercing tip and lateral aperture with an imaging obturator;

FIG. 11 is a front view in transverse cross section of a proximal portion of the imaging obturator of FIG. 10 taken along lines 11-11 to expose an X-shaped cross section thereof;

FIG. 12 is a back view in transverse cross section of a distal portion of the imaging obturator of FIG. 10 taken along lines 12-12 depicting the X-shaped cross section shaping the prolapse of tissue into the side aperture of the sleeve;

FIG. 13 is a front view in transverse cross section of a proximal portion of an alternate imaging obturator of FIG. 10, taken along lines 11-11 to expose a ridged half-cylinder cross section thereof;

FIG. 14 is a back view in transverse cross section of a distal portion of an alternate obturator of FIG. 10, taken along lines 12-12 depicting the ridged half-cylinder section, shaping the prolapse of tissue into the side aperture of the sleeve;

FIG. 15 is a right side view in elevation, taken in longitudinal cross section of an alternate imaging obturator, having an asymmetric piercing tip and having a dug-out recess capturing an MRI visible insert;

FIG. 16 is a right side view in elevation taken in longitudinal cross section of an alternate imaging obturator, having an asymmetric piercing tip and having an internal, proximally communicating cavity holding a distally positioned MRI visible insert;

FIG. 17 is a right side view in elevation taken in longitudinal cross section of an alternate imaging obturator, having an internal, proximally communicating cavity configured to draw body fluid into a dug-out recess;

FIG. 18 is a right side view in elevation taken in longitudinal cross section of the alternate imaging marker obturator of FIG. 17 after drawing tissue into the side aperture of the sleeve to present an MRI visible contour;

FIG. 23 is a right side view in elevation, taken in longitudinal cross section of an obturator having a closed, blunt distal end and a marker lumen containing an MRI visible material (e.g., gadolinium solution, aqueous solution) having an MRI dark plug (e.g., collagen, nonferrous metal, plastic) positioned and containing fluid passages to correspond to a side aperture of a sleeve;

FIG. 24 is a right side view in elevation, taken in longitudinal cross section of an obturator having a piercing distal end and a marker lumen containing an MRI visible material (e.g., gadolinium solution, aqueous solution) having an MRI dark plug (e.g., collagen, nonferrous metal, plastic) positioned and containing fluid leak passages to correspond to a side aperture of a sleeve;

FIG. 25 is a right side view in elevation, taken in longitudinal cross section of an obturator having a piercing distal end and a marker lumen containing an MRI visible material (e.g., gadolinium solution, aqueous solution) having an MRI dark plug (e.g., collagen, nonferrous metal, plastic) positioned and containing fluid passages to communicate with an obturator side aperture;

FIG. 26 is a side view in elevation of a sleeve having a notch and an open distal end with an imaging obturator shown in phantom for the MRI compatible biopsy system of FIG. 1.

FIG. 27 is a cross section view, taken along lines 27-27 perpendicular to a longitudinal axis of the sleeve of FIG. 26;

FIG. 28 is a side view in elevation of the obturator of FIG. 26 with an upper portion, which slidingly engages longitudinally a bottom portion along a dovetail joint, proximally drawn for exposing a notch in the sleeve;

FIG. 29 is a cross section view, taken along lines 29-29 perpendicular to a longitudinal axis of the obturator of FIG. 28 showing an oval-shaped sleeve lumen;

FIG. 30 is a side view in elevation of a sleeve with an integral sharp attached to a shaft having a circular cutter lumen and an underlying vacuum lumen;

FIG. 31 is a cross section view taken along line 31-31 perpendicular to a longitudinal axis of the sleeve of FIG. 30 showing a circular cutter lumen and underlying vacuum lumen;

FIG. 32 is a side view in elevation of the sleeve of FIG. 31, cut away to expose a rotatable obturator that selectively closes a notch in the sleeve;

FIG. 33 is a cross section view taken along line 33-33 perpendicular to a longitudinal axis of the sleeve of FIG. 32;

FIG. 34 is a depiction of an MRI display with the selected imaging slice passing substantially along the longitudinal length of a coaxial sleeve and obturator of FIG. 28 with the obturator in its closed position to block the notch of the sleeve;

FIG. 35 is a depiction of an MRI display with the selected imaging slice passing perpendicularly through the longitudinal length of the coaxial sleeve and obturator of FIG. 34, taken along lines 35-35;

FIG. 36 is a depiction of an MRI display with the selected imaging slice passing substantially along the longitudinal length of a coaxial sleeve and obturator of FIG. 28 with the obturator in its open position to open the notch of the sleeve;

FIG. 37 is a depiction of an MRI display with the selected imaging slice passing perpendicularly through the longitudinal length of the coaxial sleeve and obturator of FIG. 36, taken along lines 37-37;

FIG. 45 is a perspective view of a sleeve, partially cut away to expose two ports longitudinally spaced along its base with an O-ring dynamic seal therebetween and another O-ring dynamic seal, distal to both;

FIG. 46 is a cross section view along the longitudinal axis of the sleeve of FIG. 45;

FIG. 47 is a right side view in elevation, taken in longitudinal cross section of an obturator having a sharp tip shielded within a sheath;

FIG. 48 is a right side view in elevation, taken in longitudinal cross section of the obturator of FIG. 47 having a sharp tip shielded within a sheath;

FIG. 49 is a right side view in elevation taken in longitudinal cross section of an obturator, having a sharp tip selectively shielded by a split sheath that is stored within the obturator;

FIG. 49A is a front view of the obturator of FIG. 49, taken in cross section along lines 49A-49A;

FIG. 50 is a right side view in elevation, taken in longitudinal cross section of a sleeve incorporating a flap distal closure that is selectively actuated on a sleeve to shield a sharp tip;

FIG. 51 is a front view in elevation of the distal flap closure and sharp tip of the obturator and sleeve of FIG. 50;

FIG. 52 is a front view in elevation of an alternate distal flap closure with three flaps for the sleeve of FIG. 51;

FIG. 53 is a right side view in elevation, taken in longitudinal cross section of a distal portion of the sleeve of FIG. 50, with closed distal flap closure and an obturator with a protected sharp tip shown in phantom;

FIG. 54 is a front view in elevation, taken in cross section along lines 54-54 of a proximal portion of the sleeve of FIG. 50;

FIG. 61 is a right side view in elevation of a curl-biased tool rotated to deflect tip up;

FIG. 62 is a right side view in elevation taken in longitudinal cross section of a sleeve with the curl-biased tool tip extending through a side aperture of the sleeve;

FIG. 63 is a right side view in elevation of the curl-biased tool of FIG. 61 rotated a half rotation to deflect tip down;

FIG. 64 is a right side view in elevation taken in longitudinal cross section of the sleeve of FIG. 6 with the curl-biased tool tip extending through a distal opening of the sleeve;

FIGS. 72A-7D are cross sectional views of a round, oval, square/rectangular, and complex-shaped sleeve;

FIG. 74A is a front view of a perform round sleeve positioned in a forming fixture of a waisted oval mandrel inserted through the sleeve and the sleeve placed between compression plates having opposing pinching portions;

FIG. 74B is a front view of the perform round sleeve after compression and heating of the forming fixture of the compression plates against the mandrel with the perform sleeve trapped therebetween to acquire a waisted oval shape;

FIG. 74C is a front view of the waisted oval sleeve after release from the forming fixture of FIG. 74B;

FIG. 74D is a front view of a forming fixture with compression plates and mandrel shaped to constrain the perform sleeve for compression and heating in a full circumference to form a waisted oval shape;

FIG. 74E is a front view of the waisted oval shaped sleeve after release from the forming fixture of FIG. 74D;

FIG. 75 is a perspective view of a sleeve with laser formed proximal mounting holes for overmolding and side aperture;

FIG. 77 is a top diagrammatic view of a dual point flat blade attached in a slot in a conic distal piercing tip of an obturator or sleeve;

FIG. 78A is a top diagrammatic view of a primary/secondary conic piercing tip of an obturator or sleeve;

FIG. 78B is a front view in elevation of the primary/secondary conic piercing tip of FIG. 78A;

FIG. 79 is a geometric diagram of insertion torques for positive angles for the piercing tip of FIGS. 78A-78B;

FIG. 80 is a geometric diagram of insertion torques for negative angles for the piercing tip of FIGS. 78A-78B;

FIG. 81A is a perspective view of an alternate flat, triangular cutting member for a piercing portion of a sleeve or obturator;

FIG. 81B is a top view of the alternate flat, triangular cutting member of FIG. 81A;

DETAILED DESCRIPTION OF THE INVENTION

Figure 1:
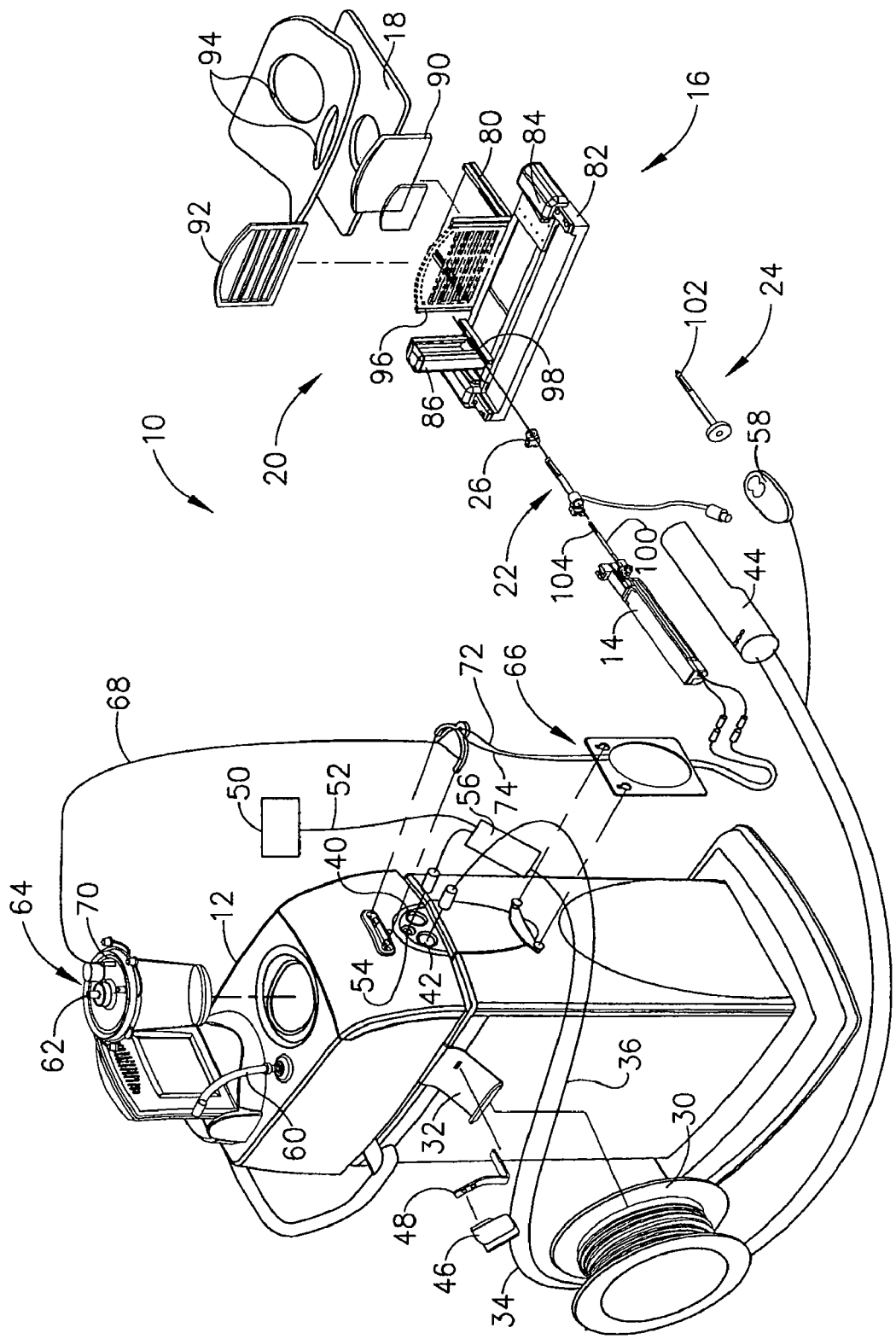
FIG. 1 is a perspective disassembled view of a Magnetic Resonance Imaging (MRI) compatible biopsy system incorporating a guided sleeve and obturator, advantageously MRI compatible and imagable, and providing therapeutic features.

Turning to the Drawings, wherein like numerals denote like components throughout the several views, in FIG. 1, a Magnetic Resonance Imaging (MRI) compatible biopsy system 10 includes a guide that guides a sleeve and introducer obturator that are separate from the biopsy device itself and advantageously incorporate an improved piercing portion, MRI imaging marker, and fluid handling capabilities. Mounting provisions allow for precise penetration along a desired trajectory without overshooting.

The MRI compatible biopsy system 10 includes a control module 12 that typically is placed outside of a shielded room containing an MRI machine (not shown) or at least spaced away to mitigate detrimental interaction with its strong magnetic field and/or sensitive radio frequency (RF) signal detection antennas. The control module 12 controls and powers an MRI biopsy device 14 that is compatible for use in close proximity to the MRI machine. An example of an MRI biopsy device 14 is the afore-mentioned MAMMOTOME™ instrument. The MRI biopsy device 14 is accurately positioned by a localization fixture 16 that is attached to a breast coil 18, which in turn supports a patient (not shown). Examples of commercially available breast coils 18 include the BIOPSY BREAST COIL MODEL BBC by MRI DEVICES CORPORATION of Waukesha Wis. A guidance assembly 20, and, in particular, a sleeve 22, advantageously attaches to the localization fixture 16 to increase imaging and therapeutic flexibility and accuracy in conjunction with selective use of the MRI biopsy device 14 during particular parts of the procedure. The guidance assembly 20 may include one or more obturators 24 with one depicted that seals the sleeve 22 during insertion and during subsequent portions of the procedure in which the MRI biopsy device 14 is not inserted therein. A depth stop 26 is provided for use with the localization fixture 16 to advantageously prevent over-insertion of the sleeve 22, inadvertent retraction of the sleeve 22 and/or to enhance accurate placement of the sleeve 22 to a desired location along the Z-Axis.

For convenience, herein a convention is used for locating a suspicious lesion by Cartesian coordinates within breast tissue referenced to the localization fixture 16 and to thereafter position an instrument (e.g., sleeve 22) to this location without necessarily continuously imaging the region. As will be described in greater detail below, a perforated barrier that is compressed along an outside side of the breast, with respect to a medial plane of the chest of the patient defines an X-Y plane, with the X-axis being vertical (sagittal) with respect to a standing patient and which corresponds to a left to right axis as viewed by a clinician facing the externally exposed portion of the localization fixture 16. A fiduciary marker (not shown)), attached to or positioned relative to the localization fixture 16 proximate to the patient's skin, defines the origin of this plane. Perpendicular to this X-Y plane and extending toward the medial side of the breast is the Z-axis, which typically corresponds to the orientation and depth of insertion of the MRI biopsy device 14, although it should be appreciated that variations may allow insertion at an angle to this Z-axis. Thus, for clarity, the term Z-axis may be used interchangeably with "axis of penetration", although the latter may or may not be orthogonal to the spatial coordinates used to locate an insertion point on the patient.

Separating the tracking rail, that supports a mount/depth stop from a biopsy rail that supports the weight of the biopsy device, advantageously reduces interference between the various components, allowing a sequence of operation wherein certain components may be selectively installed and removed without interfering with other components.

In use, the MRI compatible biopsy system 10 is prepared for use by placing a cable management spool 30 upon a cable management attachment saddle 32 that projects from a side of the control module 12. Wound upon the cable management spool 30 is a paired electrical cable 34 and mechanical cable 36 for communicating control signals and cutter rotation/advancement motions respectively. In particular, electrical and mechanical cables 34, 36 each have one end connected to respective electrical and mechanical ports 40, 42 in the control module 12 and another end connected to a holster 44 that receives the MRI biopsy device 14. An MRI docking cup 46, which may hold the holster 44 when not in use, is hooked to the control module 12 by a docking station mounting bracket 48.

An interface lock box 50, mounted to a wall, provides a tether 52 to a lockout port 54 on the control module 12. The tether 52 is advantageously, uniquely terminated and of short length to preclude inadvertent positioning of the control module 12 too close to the MRI machine. An in-line enclosure 56 may advantageously register the tether 52, electrical cable 34 and mechanical cable 36 to their respective ports 54, 40, 42 on the control module 12. A remote keypad 58 may be distally connected to the electrical cable 34 to enhance clinician control of the MRI biopsy device 14, especially when controls on the MRI biopsy device 14 itself are not readily accessible after insertion into the localization fixture 16.

Vacuum assist is provided by a first vacuum line 60 that connects between the control module 12 and an outlet port 62 of a vacuum canister 64 that catches liquid and solid debris. A tubing kit 66 completes the pneumatic communication between the control module 12 and the MRI biopsy device 14. In particular, a second vacuum line 68 is connected to an inlet port 70 of the vacuum canister 64. The second vacuum line 68 divides into two vacuum lines 72, 74 that are attached to the MRI biopsy device 14. With the MRI biopsy device 14 installed in the holster 44, the control module 12 performs a functional check. Saline is manually injected into biopsy device 14 to serve as a lubricant and to assist in achieving a vacuum seal. The control module 12 actuates a cutter mechanism (not shown) in the MRI biopsy device 14, monitoring full travel.

The portion of the MRI compatible biopsy system 10 used near the MRI machine is also assembled. The generally known breast coil 18 is placed upon a gantry of the MRI machine, along with other body support pads (not shown). The localization fixture 16, which is attached within a recess on either lateral side of the breast coil 18 to access a patient's breast that is pendulously exposed therein, includes a horizontal medial plate 80, a reusable base assembly 82, a lateral assembly 84, and a positioning pedestal 86. The localization fixture 16 is also assembled with a disposable medial fence 90 and a lateral window (or perforated plate) 92.

The base assembly 82 is placed within a selected lateral recess of the breast coil 18. The medial fence 90 attaches to a medial edge of the medial plate 80, aligned vertically approximately along a longitudinal axis of the breast coil 18 under an inner edge of a selected breast aperture 94 that receives a patient's breast. With the patient thus positioned and the outer area of the breast sterilized, the lateral window 92 is downwardly slid into a three-sided frame guide 96 of the lateral assembly 84, which in turn is placed upon the medical plate 80. The base assembly 82 and lateral assembly 84 are moved with respect to one another along the Z-axis to compress the patient's breast between the medial fence 90 and the lateral window 92. A mechanism formed between the lateral assembly 84, base assembly 82, and medial plate 80 maintains this compression.

Contrast agent may be injected into the patient to enhance the imaging. The gantry is advanced into the MRI machine bore to image the localization fixture 16 and breast tissue. The fiduciary marker on the lateral window 92 is located and designated as the origin of the X-Y-Z coordinates. Then a suspicious lesion is located within the image and a point thereon selected to determine its location relative to the origin. It should be appreciated that orienting the X-Y-Z axis of an initial scan may be facilitated by having the lateral window 92 formed of an imagable material, thus presenting an X-Y plane in addition to the origin point of the fiduciary marker. With the target location determined, the gantry is withdrawn from the MRI machine bore.

The positioning pedestal 86 is slidably engaged along the X-axis of the lateral assembly 84 and defines a vertical guide for positioning a single targeting rail ("track") 98 at a selected Y-axis coordinate. The track 98 in turn provides a depth guide along the Z-axis for positioning the depth stop 26 and the holster 44 at a desired Z-axis coordinate. The depth stop 26 is latched onto the track 98. Thereafter, a marking instrument (not shown) may be inserted through the depth stop 26 to mark the insertion point on the breast. Thereafter, the depth stop 26 is moved out of the way. Anesthesia is injected superficially, followed by a scoring cut at the marked location and a subsequent injection of anesthesia more deeply into the scored cut. The depth stop 26 is then repositioned on the track 98 to the desired Z-axis coordinate reference.

The obturator 24 is inserted into the sleeve 22 and may be positioned to close any apertures of the sleeve 22 (side and/or distal end) to present a closed surface to the breast tissue. The obturator may also be shaped or formed to enhance the visibility of the aperture location. One or the other of the obturator 24 and sleeve 22 presents a sharp tip (not shown) to penetrate breast tissue. For instance, if using a sleeve 22 having an open end, an obturator may provide a sharp tip.

The obturator 24 is inserted into the sleeve 22 and the combination is guided by the track 98 to a proper orientation until an accurate depth is reached as set by the depth stop 26. Once fully inserted, the depth stop 26 prevents over-insertion. The sleeve 22 advantageously latches to the track 98 and/or the depth stop 26 to prevent inadvertent retraction, such as when the obturator 24 is withdrawn, and pressure is received from the breast tissue or later when a probe 100 of the MRI biopsy device 14 is withdrawn from the sleeve 22.

The gantry is moved into the MRI machine bore and the patient is imaged again to confirm placement of the sleeve 22 with respect to the suspicious lesion. Advantageously, imagable materials of the sleeve 22 and/or obturator 24, perhaps comprising or including marker material, enhance the ability to confirm the location of the sleeve 22 and its sleeve side aperture 102 as positioned for subsequent biopsy samples.

Figure 2:
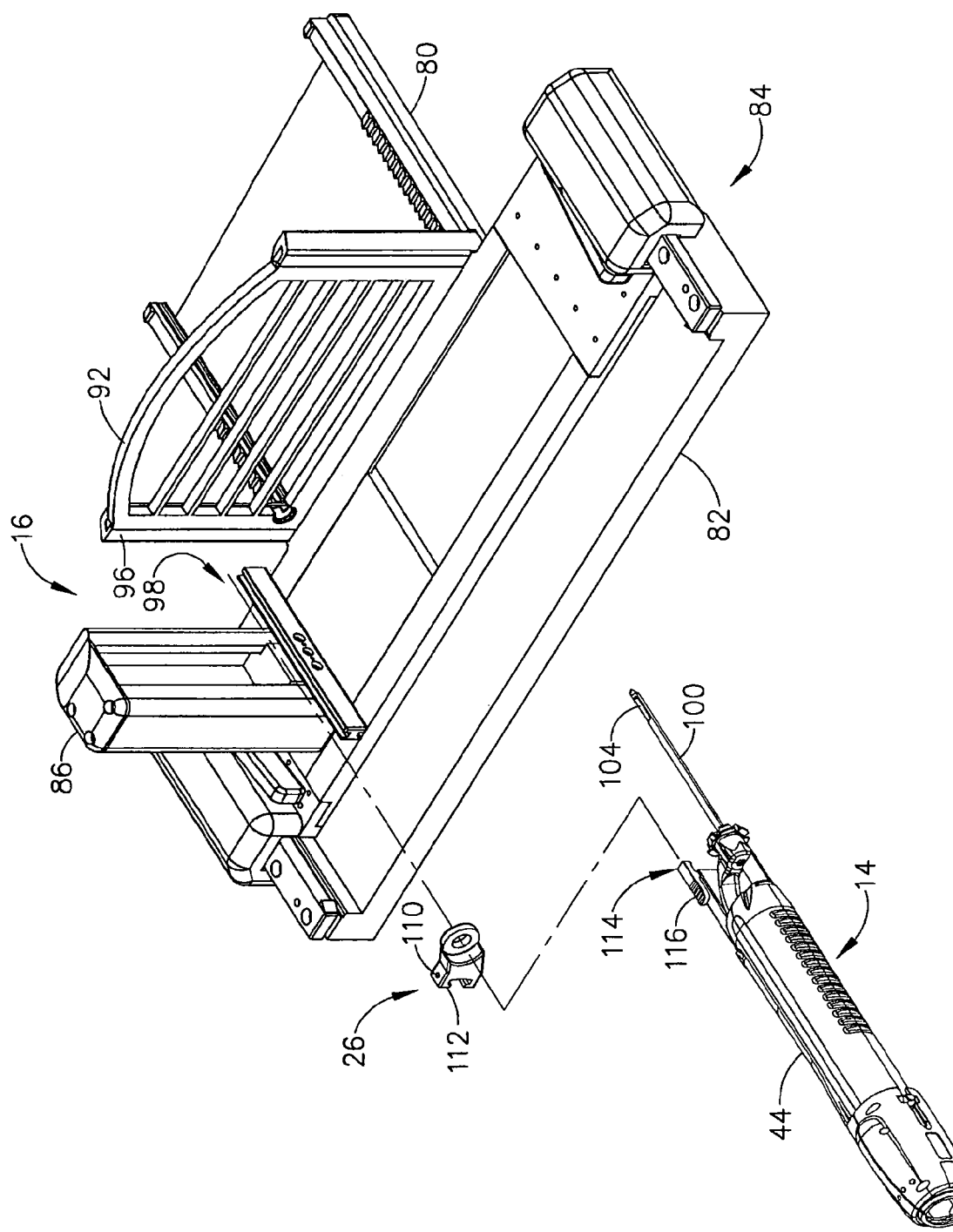
FIG. 2 is a disassembled perspective view of a guidance portion of a localization fixture and a disassembled MRI biopsy device of the MRI compatible biopsy system of FIG. 1.
Figure 3:
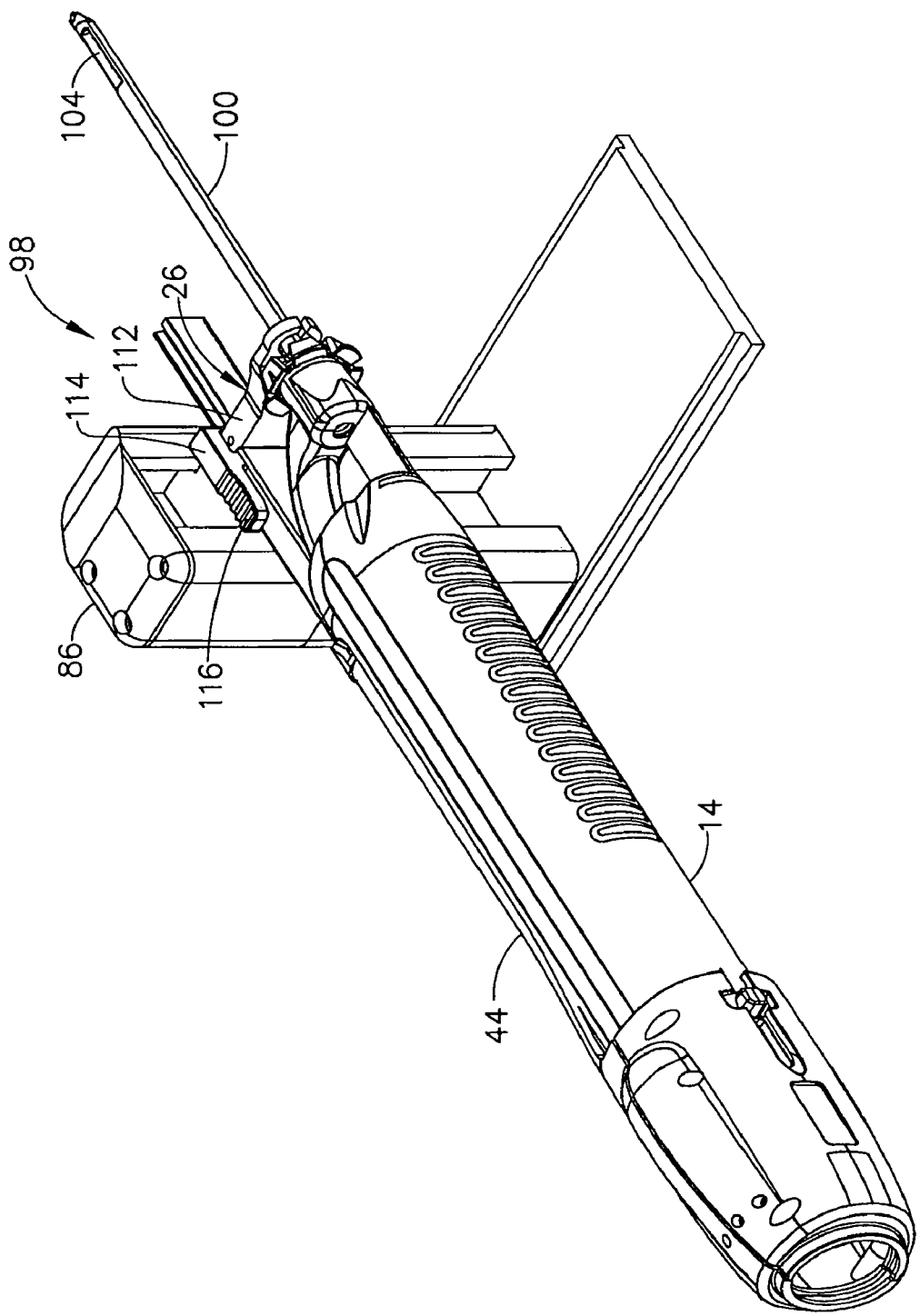
FIG. 3 is a perspective view of the MRI biopsy device of FIG. 2, mounted on the guidance portion of the localization fixture.

The patient is removed from the MRI machine by retracting the gantry and the holstered MRI biopsy device 14 is brought to the localization fixture 16. A protective cap (not shown) is removed from the probe 100 of the MRI biopsy device 14 and the obturator 24 is removed from the sleeve 22. Mounting of the holster 44 to the track 98 is shown in FIGS. 2 and 3, wherein the holster 44 and MRI biopsy device 14 combination slide onto the track 98 that has been positioned at a certain location with respect to the pedestal 86 and lateral assembly 84. Features of the sleeve 22 and probe 100 may advantageously visually and mechanically orient a probe side aperture 104 of the probe 100 with the sleeve side aperture 102, as well as forming a gas seal. Advantageously, the holster 44 and/or the probe 100 may latch onto the track 98 or sleeve 22 to confirm full insertion and prevent over-insertion and inadvertent retraction. The holster 44 allows an MRI biopsy device 14, intended for handheld use, to have sufficient support in its attachment to the localization fixture 16 to accurately maintain its position and to avoid or minimize loads carried by the probe 100.

Thereafter, the MRI compatible biopsy system 10 may take tissue samples by activating a cutter mechanism in conjunction with vacuum assist, withdrawing the cutter and withdrawing a tissue sample, the latter perhaps also with vacuum assist. The probe 100/sleeve 22 combination is capable of manual, or perhaps automatic, rotation to a desired angle with respect to their longitudinal axis for additional samples or additional samples may be taken at the current orientation by further resorting to vacuum assist. The cutter is then advanced to close the probe side aperture 104 and the holster 44 is withdrawn from the localization fixture 16, thereby removing the probe 100 from the sleeve 22.

Additional steps or combinations of steps may be performed at this point, such as using the probe 100, a specialized obturator 24 (e.g., stylet), or merely the sleeve 22 to guide various agents to the surgical site of the biopsy. Examples include draining fluids, inserting anesthetic agents, inserting hemostatic agents, insulating with pneumatic pressure and inserting a marker for subsequently locating the site of the biopsy, or other diagnostic or therapeutic procedures.

The patient is then typically drawn back into the MRI machine bore for reimaging to confirm removal of at least a portion of the suspicious lesion and possibly placement of a marker. During this reimaging, the sleeve 22 is sealed with the obturator or stylet 24. Thereafter, the localization fixture 16 is removed, the patient is bandaged and removed from the gantry, and the disposable portions of the MRI compatible biopsy system 10 are disposed of as medical waste.

With particular reference to FIGS. 2-3, the single targeting rail 98 facilitates sequential mounting of separate components. First, the depth stop 26, then the sleeve 22 (as in FIG. 1), and then the biopsy tool 14 is slid onto the single targeting rail 98. Alternatively as depicted in FIGS. 2-3, the single targeting rail 98 may receive the depth stop 26 and then an MRI biopsy device 14 is used without a separate sleeve 22. The maximum depth of penetration into the patient's breast is preset by the location of the depth stop 26 on the single targeting rail 98. An engagement mechanism between the holster 44 and the single targeting rail 98 (not shown) and/or an engagement mechanism formed by a catch, depicted as an upwardly projecting pin 110, on an upper rail-gripping arm 112 of the depth stop 26 and a downwardly spring-biased rocker latch 114 that snaps onto the upwardly projecting pin 110, preventing inadvertent retraction of the MRI biopsy device 14. The holster 44 may be disengaged by downward pressure on a proximal actuating arm 116 of the rocker latch 114.

The single targeting rail 98 may be longitudinally sized to extend proximally sufficiently so that the MRI biopsy device 14 engages the single targeting rail 98 prior to the probe 100 contacting the patient's skin. The single targeting rail 98 is also sized to not extend proximally to the extent that it would preclude use in a closed bore MRI machine (not shown). Such an MRI compatible biopsy system 10 is believed to minimize the procedure turn-around time to less than 45 minutes as described above. However, despite the expeditious turn-around, a radiologist may position the probe 100 accurately to within 2 mm (5 mm maximum) of the lesion center. Further, the radiologist may maximize access to both breasts (left or right) during a procedure (both sides of the table) with minimal repositioning of the patient. Further, a minimal amount of force is needed to penetrate tissue, such as less than 4 lbs. Although the depth stop 26 serves to prevent overshooting, features for repositioning the depth stop 26 prior to further insertion of the probe 100 allow clinical flexibility in targeting another location.

Figure 4:
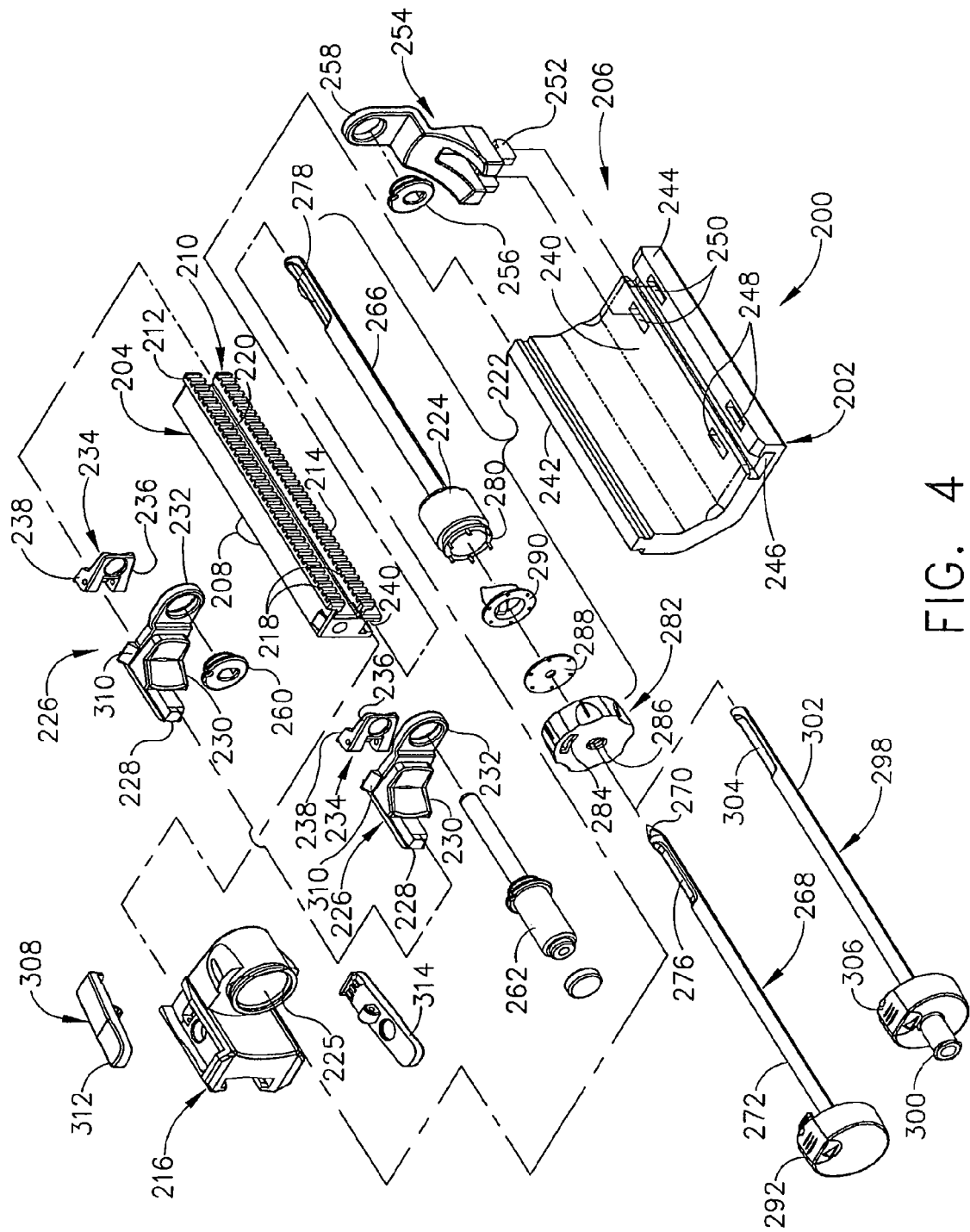
FIG. 4 is a perspective disassembled view of an alternative guidance portion, including a cradle supporting a sleeve having open distal end and side aperture, an imaging obturator with a piercing tip, and a fluid communicating stylet that is also used to place a marker for the MRI compatible biopsy system of FIG. 1.

In FIG. 4, an alternative guidance assembly 200 for the MRI compatible biopsy system 10 incorporates a cradle 202 that attaches to a targeting rail 204 and provides a biopsy rail 206 for supporting the MRI biopsy device 14, both rails 204, 206 aligned to the Z axis. The targeting rail 204 is attached to the positioning pillar 86 (not shown in FIG. 4) and is vertically adjusted to a desired Y-position. A circular attachment point 208 may form a rotational engagement to the positional pedestal 86 to allow an angled targeting guide.

A lateral face 210 of the targeting rail 204 includes an upper flange 212 and a lower flange 214, each having an L-shaped cross section for slidingly receiving a sleeve mount 216. Vertical rows of laterally projecting ridges 218 in each flange 212, 214 serve as a locking surface for the sleeve mount 216. Between the flanges 212, 214, a side channel 220 is recessed therein. The sleeve mount 216 guides a sleeve 222 by having its sleeve hub 224 proximally received in a hub receptacle 225 of the sleeve mount 216 and is distally positioned and constrained by a depth stop 226.

The depth stop 226 includes a slide member 228 that engages the side channel 220. A depth stop housing 230 attaches thereto, terminating in a reticule 232. A locking lever 234 is vertically pinned within a distally open recess (not shown), defined in the depth stop 226 with a lateral portion 236 spring biased away therefrom such that distally projecting feet 238 pivot against and engage the ridges 218, especially against a proximal movement. Depressing the lateral portion 236 proximally against the distally open recess of the depth stop housing 230 releases the distally projecting feet 238 to allow repositioning the depth stop 226 distally.

An axis of penetration of the biopsy device 14 is aligned with the axes defined by the targeting rail 204 and the biopsy rail 206, which are laterally and vertically orthogonally offset therefrom, respectively. Extending a horizontal plane from the targeting rail 204 and extending a vertical plane from the biopsy rail 206 intersect at a common centerline that is the axis of penetration. Having the biopsy rail 206 vertically aligned and parallel to the axis of penetration advantageously provides support for the weight of the biopsy device 14 with a minimum of torsion loads that may otherwise create deflections of an inserted distal end. Thereby, even for a relatively heavy and elongated device, positioning and maintaining its distal end is achievable within 5 mm, and even 2 mm, of a desired insertion point. Thereby, a "hands free" procedure may be performed. As an alternative, the cradle 202 below the axis of penetration pedestal 86 in the illustrative version may be replaced by one vertically displaced above the axis of penetration.

While a "hands free" capability is advantageous for a single insertion/multiple sample biopsy device, it should be appreciated that such penetration guidance with a preset depth stop as described herein has application to even lightweight biopsy devices that employ a core needle biopsy with a single insertion per single sample. In particular, correct placement need not be conditional on continuous imaging. Over penetration during insertion and inadvertent displacement is avoided when hands are free.

A bottom dovetail channel 240 in the targeting rail 204 receives a top dovetail extension 242 on the cradle 202, which is slid therein. It should be appreciated that mounting is shown herein on the right side of the positioning pedestal 86 when viewed proximally, but that the guidance assembly 200 advantageously comprises symmetric parts that allow mounting and use on either side of the positioning pedestal 86 to increase flexibility in positioning the probe 100. Thus, a horizontal base 244 of the cradle 202 forms the biopsy rail 206 as a biopsy guide channel 246 flanked by a first and second pair of monocle receptacles 248, 250 so that a pair of locking hooks 252 on a monocle 254 may be inserted in either pair of monocle receptacles 248, 250, depending on which is closer to the patient. Rather than mounting the cradle 202 to the targeting rail 204 as depicted, a cradle may be directly attached to the positioning pedestal 86 (not shown). The cradle 202 is mechanically robust and can support the gross weight of the MRI biopsy device 14. Since the MRI biopsy device 14 does not share the cradle 202, the cradle 202 may be optimized to support the MRI biopsy device 14 when either shallow or deep lesions need to be accessed.

A guide bushing 256 inserted in a monocle reticule 258 guides a marking instrument and/or a scoring scalpel (not shown) as an initial step in locating and preparing an insertion point. The monocle 254 may be removed thereafter or left in place to guide the sleeve 222 in addition to the reticule 232 of the depth stop 226, the latter which may also hold a guide bushing 260 for guiding the sleeve 222. Removing the guide bushings 256, 260 allows for the reticules 258, 232 of the monocle 254 and depth stop 226 to guide a larger component, such as a fiducial 262 used for locating a suspicious lesion relative to the guidance assembly 200.

The alignment of the sleeve 222 is maintained by first passing through the hub receptacle 225 of the sleeve mount 216, which receives the sleeve hub 224. In the illustrative version, the sleeve 222 has an open ended shaft 266 for receiving an introducer obturator 268 that includes a piercing tip (e.g., flat blade) 270 at a distal end of solid obturator shaft 272. A beveled recess 276 into the solid obturator shaft 272 is aligned with a sleeve side aperture 278 of the sleeve 222, and thus ultimately of the probe 100 (FIGS. 1-3). The materials of the obturator 268 may be selected to aid in locating the sleeve side aperture 278 of the sleeve 222, which otherwise may be more difficult to visualize and locate in an MRI scan slice.

The sleeve hub 224 has its proximal cylindrical edge 280 attached to a guidance thumbwheel 282 that proximally extends from the hub receptacle 225 of the sleeve mount 216 for rotating the sleeve 222 to position its sleeve side aperture 278 with reference to a visual mark, depicted as a locking slot 284, on the thumbwheel 282 corresponding thereto. The thumbwheel 282 includes a central through hole 286 sealed by a wiper seal 288 and a duckbill seal 290 trapped between the thumbwheel 282 and the proximal cylindrical edge 280 of the sleeve hub 224. Thus, insertion of the obturator 268, which includes a locking tab 292 that enters the locking slot 284, closes the central through hole 286 and forms a dynamic seal against the wiper seal 288.

After removing the obturator 268, a stylet 298 may be inserted into the sleeve 222 so that a proximally presented hose nib 300 of the stylet 298 may be used to insufflate the surgical site or used for other purposes such as draining bodily fluids or inserting therapeutic or diagnostic agents through a stylet shaft 302 of the stylet 298 to a stylet side aperture 304 that is aligned with the side aperture 278 of the sleeve 222. The stylet 298 also includes a locking tab 306.

The sleeve mount 216 includes a downwardly spring-biased rocker latch 308 that snaps onto a ramped catch 310 on the depth stop 226, preventing inadvertent retraction of the sleeve 222. The sleeve mount 216 may be disengaged by downward pressure on a proximal actuating arm 312 of the rocker latch 308. An upwardly spring-based rocker latch 314, attached to the bottom of the sleeve mount 216, similarly engages the depth stop 226. Thus, after the depth stop 226 is set on the targeting rail 204 to a desired depth of insertion, the sleeve mount 216 may be distally advanced without overshooting and subsequently may be held in place when removing implements therefrom such as the obturator 268, stylet 298, and MRI biopsy device 14.

Figure 5:
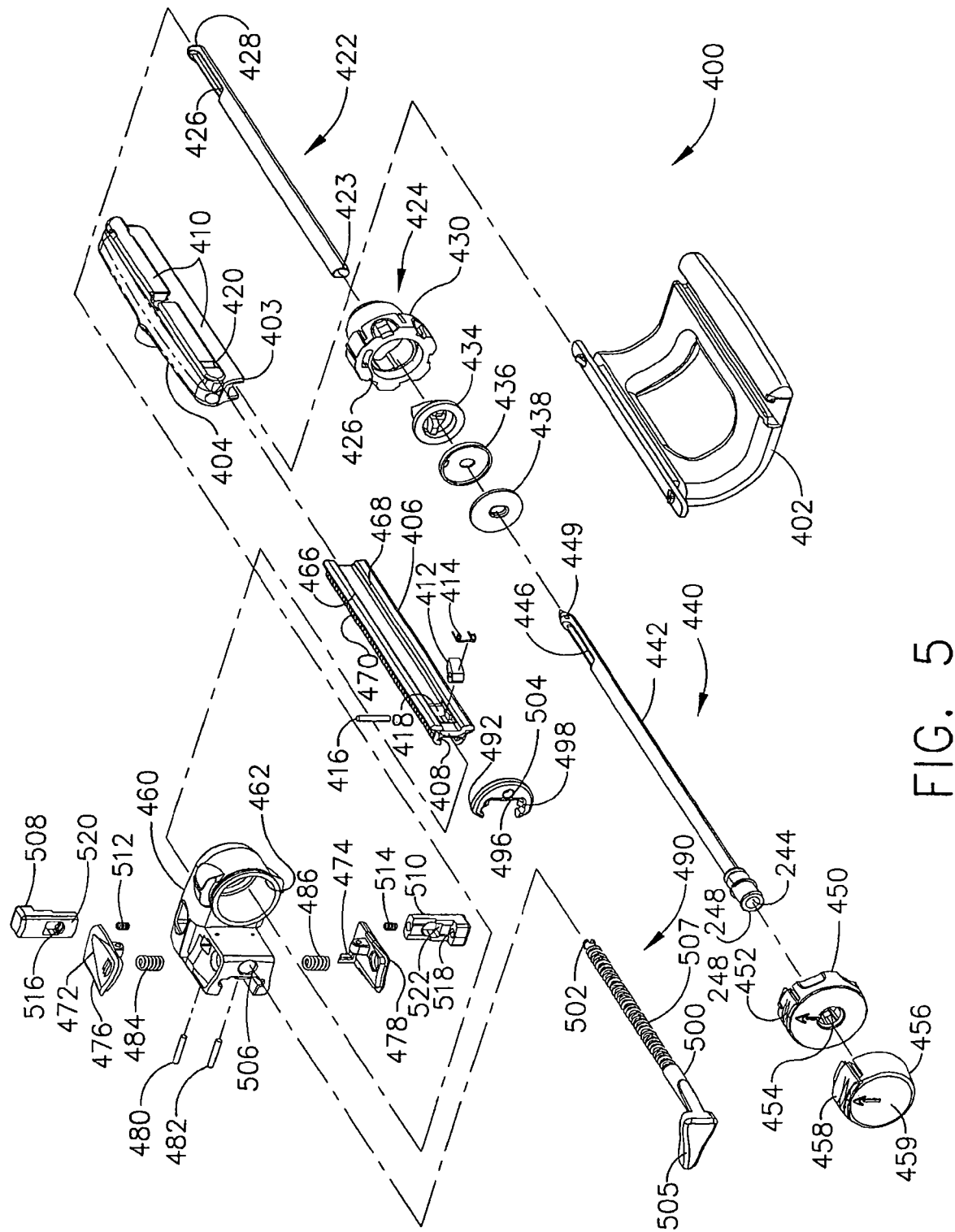
FIG. 5 is a perspective disassembled view of a further alternative guidance assembly supporting a sleeve with an imaging/marking obturator having a fluid lumen and piercing tip.

In FIG. 5, a further alternative guidance assembly 400 for the MRI compatible biopsy system 10 includes a cradle 402 that engages a bottom channel 403 of a primary targeting rail 404. To provide additional guidance to the MRI biopsy device 14 of FIGS. 1-3, a secondary targeting rail 406 includes a lateral channel 408 that is guided along a longitudinal guide tab 410 of the primary targeting rail 404. When fully engaged thereon, a pawl 412, pivoting under urging of a pawl spring 414 about a vertical pawl pin 416 in a lateral window 418 proximally positioned in the secondary targeting rail 406, drops into a proximal detent 420 proximally positioned on the primary targeting rail 404.

A sleeve 422 includes a hollow shaft (or cannula) 423 that is proximally attached to a cylindrical hub 424 and has a lateral aperture 426 proximate to an open distal end 428. The cylindrical hub 424 has an exteriorly presented thumbwheel 430 for rotating the lateral aperture 426. The cylindrical hub 424 has an interior recess 432 that encompasses a duckbill seal 434, wiper seal 436 and a seal retainer 438 to provide a fluid seal when the shaft 423 is empty and to seal to an inserted introducer obturator 440.

The introducer 440 advantageously incorporates a number of components with corresponding features. A hollow shaft 442 includes a fluid lumen 444 that communicates between a side opening 446 and a proximal port 448. The hollow shaft 442 is longitudinally sized to extend a piercing tip 449, when fully engaged, out of the distal end 428 of the sleeve 422. An obturator thumbwheel cap 450 encompasses the proximal port 448 and includes a locking feature 452, which includes a visible angle indicator 454, that engages the sleeve thumbwheel 430 to ensure that the side opening 446 is registered to the lateral aperture 426 in the sleeve 422. An obturator seal cap 456 may be engaged proximally into the obturator thumbwheel cap 450 to close the fluid lumen 444. The obturator seal cap 456 includes a locking feature 458 that includes a visible angle indicator 459 that corresponds with the visible angle indicator 454 on the obturator thumbwheel cap 450.

The sleeve 422 is guided, during penetration of tissue, by a sleeve mount 460 having a sleeve hub 462 that receives the cylindrical hub 424 of the sleeve 422. The sleeve mount 460 has a lateral sleeve hub channel 464 that slides along top and bottom guide flanges 466, 468 of the secondary targeting rail 406, each having an aligned and recess ridged, ratcheting surface 470 that interacts with a respective top and bottom ratcheting feature 472, 474 on respective top and bottom rail lock rocker latches 476, 478 that are engaged by respective top and bottom latch pins 480, 482 in respective sides of the sleeve mount 460. The ratcheting features 472, 474 are proximally ramped such as to allow distal movement. Distal portions of each rail lock rocker latches 476, 478 are biased away from the sleeve mount 460 by respective rail lock compression springs 484, 486 to bias the ratcheting features 472, 474 into contact with the ridges surfaces 470 of the guide flanges 466, 468. Simultaneous depression of the rail lock rocker latches 476, 478 allow the sleeve mount 460 to be drawn proximally, withdrawing any sleeve 422 supported therein, until the sleeve mount 460 reaches a proximal end of the secondary targeting rail 406, whereupon the sleeve mount 460 rotates the pawl 412 clockwise (as viewed from the top) and is thus engaged to the secondary targeting rail 406 as the secondary targeting rail 406 is unlocked from the primary targeting rail 404, causing removal therefrom with continued proximal movement.

Before mounting the secondary targeting rail 406 onto the primary targeting rail 404 in the first place, the sleeve mount 460 is advantageously adjustably positioned on the secondary targeting rail 406 to set a desired depth of penetration. In particular, a depth guide 490 is formed by a crescent-shaped depth indicator 492 having a lateral channel 496 shaped to engage the top and bottom guide flanges 466, 468. Forward ramped surfaces 498 on the top and bottom of the lateral channel 496 are positioned to engage the ridged ratcheting surfaces 470 on the secondary targeting rail 406, allowing assembly by inserting the depth indicator 492 from a distal end of the secondary targeting rail 406. Frictional engagement thereafter resists further proximal movement and strongly opposes any distal movement, especially from a depth lead screw 500 of the depth guide 490, whose distal end 502 rotates within an outboard hole 504 in the depth indicator 492 and whose proximal end deflects laterally as a depth actuator lever 505 is used to rotate and longitudinally position the depth lead screw 500 therein. A mid portion of the depth lead screw 500 is received in a longitudinal through hole 506 formed in the sleeve mount 460 outboard to its lateral channel 408. For coarse depth adjustment, outer lead threads 507 on the depth lead screw 500 selectively engage the sleeve mount 460 until top and bottom coarse adjust buttons 508, 510 are inwardly depressed into the sleeve mount 460, compressing respective top and bottom coarse adjust compression springs 512, 514. Each coarse adjust button 508, 510 includes a respective vertically elongate aperture 516, 518 whose inward surface presents a worm gear segment 520, 522 to engage the outer lead threads 507 on the depth lead screw 500 when urged into engagement by relaxed coarse adjust compression screws 512, 514.

In two U.S. patent applications entitled "AN MRI COMPATIBLE BIOPSY DEVICE WITH DETACHABLE PROBE", to Hibner et al., Serial In the above-referenced U.S. patent application Ser. No. 10/170,535, filed on 23 Apr. 2002, and published on 23 Oct. 2003 as Pub. No. US 2003/0199753, and entitled "MRI BIOPSY DEVICE", Ser. No. 11/076,612, filed 10 Mar. 2005, the disclosure of both of which are hereby incorporated by reference in its entirety, a detachable probe (or sleeve) is described that has a number of advantages, such as allowing MRI procedures to be performed with the probe remaining inserted during reimaging. In FIGS. 1-5, a separate sleeve and obturator capability provides even additional clinical flexibility. It should be appreciated, that various combinations of features may be selected for specific applications or preferences. Having a side aperture in a sleeve, corresponding to a sample-taking side aperture in the biopsy device, is often desirable. For instance, an open ended probe or biopsy needle that is inserted by necessity into a suspicious lesion may create hematomas that fill with residual contrast agent making it difficult to perform further imaging studies at that site. For another, piercing a suspicious lesion may pose a risk of track metastasis. Further, the tip of such a needle or probe may be difficult to image with respect to the suspicious lesion to accurately locate the latter, being essentially a point.

Figure 6:
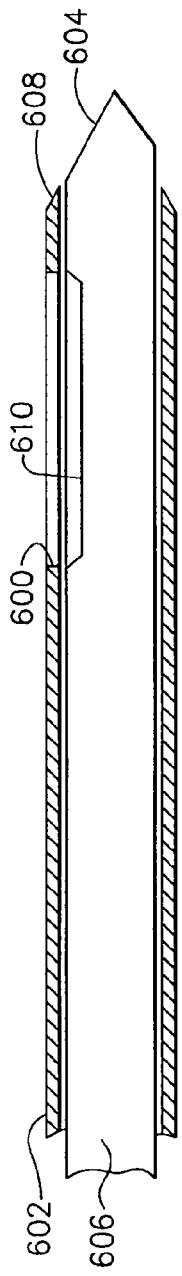
FIG. 6 is a right side diagrammatic view in elevation taken in longitudinal cross section of the sleeve with an open distal end and lateral aperture and introducer, imaging obturator of FIG. 5 with the obturator having a dug-out marker recess.

By contrast, in FIG. 6, a side aperture 600 of a sleeve 602 may be positioned beside a suspicious lesion so that a piercing tip 604 need not pass through the suspicious lesion. Locating this side aperture 600 in an MRI scan slice would seem to be easier in that the side aperture 600 defines a line that more readily allows orienting an imaging slice along its length with a geometric reference that readily shows from what direction tissue may be drawn into the side aperture 600 for biopsying. However, slices that are not ideally oriented or that pass through MRI compatible materials that may form the sleeve 602 may still complicate accurate and expedient identification of the side aperture 600. To assist in this identification, an obturator 606 assists during introduction of the sleeve 602 by substantially or completely blocking the side aperture 600 so that tissue does not prolapse into the side aperture 600 and impede insertion and/or cause tissue trauma.

In some applications, it is further desirable to have a distal opening 608 in the sleeve 602. The obturator 606 thus advantageously includes the piercing tip 604 that extends distally out of the distal opening 608 in the sleeve 602. The obturator 606 further has a lateral recess (e.g., notch, bevel, canoe dug-out) 610 aligned with the side aperture 600 in the sleeve 602 when the obturator 606 is fully inserted therein. Being radially asymmetric, this lateral recess 610 provides a rapidly acquired and interpreted reference for locating the side aperture 600.

Figure 7:
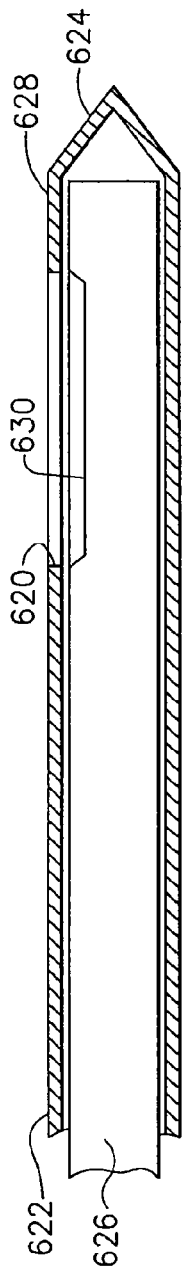
FIG. 7 is a right side diagrammatic view in elevation, taken in longitudinal cross section of a sleeve with a side aperture and piercing tip used with an introducer, imaging obturator having a dug-out marker recess for the MRI compatible biopsy system of FIG. 1.

In FIG. 7, a side aperture 620 is formed in a sleeve 622 that has a closed distal end 628 that forms or supports a piercing tip 624. An obturator 626 serves to shape the prolapse of tissue into the side aperture 600 during introduction and includes a lateral recess (e.g., notch, bevel, canoe dug-out) 630 aligned with the side aperture 620 in the sleeve 622 when the obturator 626 is fully inserted therein.

Figure 8:
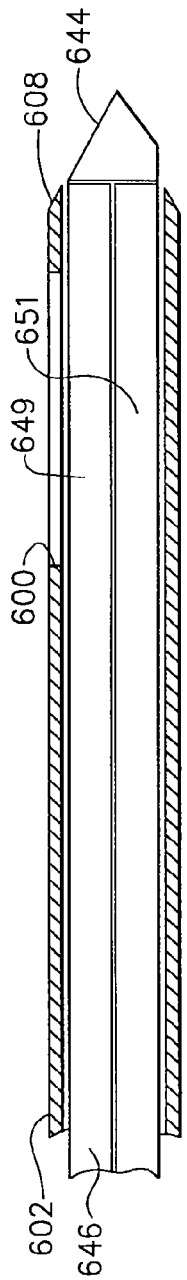
FIG. 8 is a right side diagrammatic view in elevation taken in longitudinal cross section of a sleeve with a lateral aperture and open distal end used with an introducer, imaging obturator having a non-cylindrical cross section and piercing tip for the MRI compatible biopsy system of FIG. 1.

In FIG. 8, an obturator 646 includes a piercing tip 644 that extends out of the distal opening 608 in the sleeve 602 of FIG. 6. The obturator 646 creates a distinctive cross section by having an upper longitudinal portion 649 and a lower longitudinal portion 651. The upper longitudinal portion 649 is shaped to control the prolapse of tissue into the side aperture 600 as well as present a readily located reference for an MRI scan slice.

Figure 9:
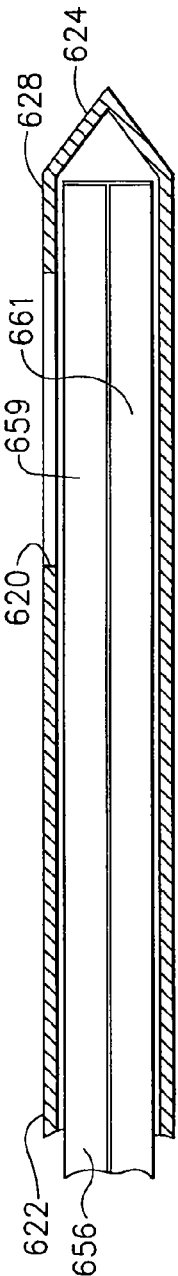
FIG. 9 is a right side diagrammatic view in elevation taken in longitudinal cross section of the sleeve of FIG. 7 with an introducer, imaging obturator having a non-cylindrical cross section for the MRI compatible biopsy system of FIG. 1.

In FIG. 9, the sleeve 622 of FIG. 7, with the closed distal end 628 formed into or supporting the piercing tip 624, is shown having its side aperture 620 closed during introduction by an obturator 656 having a distinctive cross section showing an upper longitudinal portion 659 and a lower longitudinal portion 661. The upper longitudinal portion 649 has a cross sectional profile that is designed to shape the prolapse of tissue into the side aperture 620 as well as present a readily located reference for an MRI scan slice.

In FIG. 10, a sleeve 702 has a side aperture 700 and a closed distal end 708 which are formed into an asymmetric piercing tip 704 that encompasses an obturator 706. The obturator 706 has a continuous profile formed by an upper longitudinal portion 709 and a lower longitudinal portion 711 that create a distinctive cross section, such as an X-shape as depicted in FIGS. 11-12. Alternatively, the obturator 706 may have a distinctive cross section such as an upward longitudinal spine 715 attached to a lower longitudinal half-cylinder 717 as depicted in FIGS. 13-14. It should be appreciated that the prolapse of tissue at the side aperture 700 provides an MRI image return whereas in other portions of the obturator 706, the air spaces between the sleeve 702 and the obturator 706 appear similarly dark.

In FIG. 15, an obturator 806 includes a lateral notch 810 proximate to a piercing tip 804. Rather than relying upon tissue prolapsing under forces of gravity, palpation or vacuum assist, an MRI visible insert 807 (e.g., an aqueous gel) may advantageously have sufficient stiffness to remain in place and to prevent prolapse of tissue into a side aperture of a sleeve (not shown in FIG. 15). In FIG. 16, instead of being laterally inserted, an obturator 826 may include a proximally accessed marker lumen 827 through which a marker insert 829 may be inserted proximate to a distal piercing tip 824.

Figure 19:
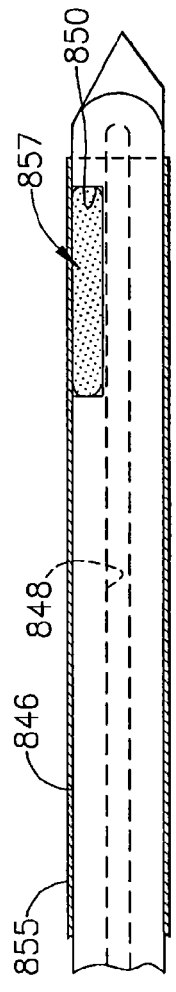
FIG. 19 is a right side view in elevation, taken in longitudinal cross section of the alternate imaging marker obturator of FIG. 17 with an MRI visible material contained within a sheath-covered lateral notch.

As an alternative to an added MRI visible material, in FIG. 17, an obturator 846 includes a vacuum lumen 848 that communicates with a lateral notch 850 to draw in sufficient bodily fluids 851 to present an MRI visible image of the side aperture of the sleeve (not shown). In FIG. 18, the obturator 846 employs vacuum assist through the vacuum lumen 848 to prolapse tissue 853 into the lateral notch 850 to present an MRI visible image. In FIG. 19, the obturator 846 further includes a thin sheath 855 that is slid overtop of the lateral notch 850 to capture an MRI visible material (e.g., aqueous fluid, gadolinium solution, etc.) 857.

Figure 20:
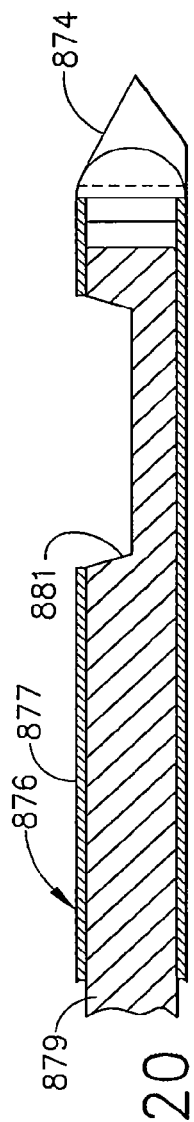
FIG. 20 is a right side view in elevation taken in longitudinal cross section of an assembled imaging marker obturator, including a solid stylet having a lateral notch and encompassed by a penetrating sheath with a molded, asymmetric piercing tip.

In FIG. 20, an obturator 876 includes a solid stylet insert 879 substantially encompassed by a cylindrical sheath 877, except for over a lateral notch 881 formed in the solid stylet insert 879. The cylindrical sheath 877 is distally attached to a ceramic asymmetric piercing tip 874.

Figure 21:
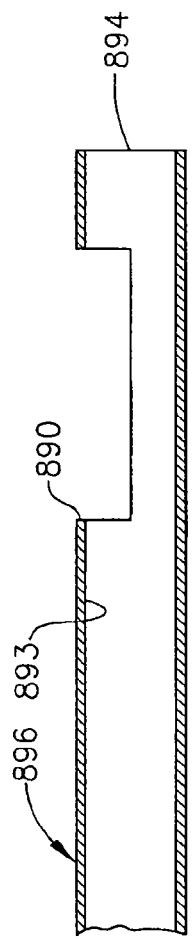
FIG. 21 is a right side view in elevation, taken in longitudinal cross section of an obturator, having an open distal end and a lateral aperture with vacuum assisted air evacuation to allow a marker lumen to fill with bodily fluids to present an MRI visible material.

In FIG. 21, an obturator 896 has an open distal end 894 and a lateral aperture 890 with vacuum assisted air evacuation proximally from a marker lumen 893 formed therein, allowing the marker lumen 893 to fill with bodily fluids to present an MRI visible material.

Figure 22:
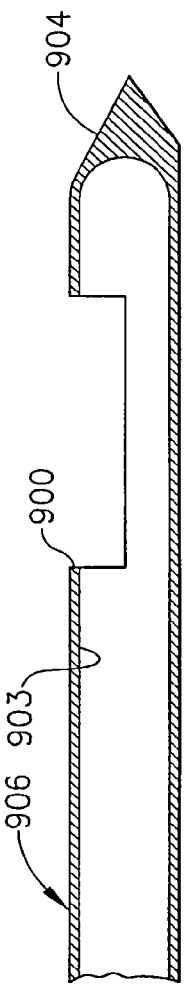
FIG. 22 is a right side view in elevation, taken in longitudinal cross section of an obturator having a piercing distal end and a lateral aperture with vacuum assisted air evacuation to allow a marker lumen to fill with bodily fluids to present an MRI visible material.

In FIG. 22, an obturator 906 has a piercing distal end 0904 and a lateral aperture 0900 with vacuum assisted air evacuation to allow a marker lumen 903 to fill with bodily fluids to present an MRI visible material.

In FIG. 23, an obturator 916 has a closed, blunt distal end 914 and a marker lumen 918 containing an MRI visible material (e.g., gadolinium solution, aqueous solution) 911. An MRI dark plug 913 (e.g., collagen, nonferrous metal, plastic) is positioned to correspond to a side aperture of a sleeve (not shown in FIG. 23). The MRI dark plug 913 contains longitudinal fluid leak passages 915 to allow MRI bright images to be formed to each side of the side aperture within the marker lumen 918.

In FIG. 24, an obturator 926 has a piercing distal end 924 and a marker lumen 928 containing an MRI visible material (e.g., gadolinium solution, aqueous solution) 921. An MRI dark plug (e.g., collagen, nonferrous metal, plastic) 923 is positioned to correspond to a side aperture of a sleeve (not shown in FIG. 24). The MRI dark plug 923 contains longitudinal fluid leak passages 925 to allow MRI bright images to be formed to each side of the side aperture within the marker lumen 928.

In FIG. 25, an obturator 936 has a piercing distal end 934 and a marker lumen 938 containing an MRI visible material (e.g., gadolinium solution, aqueous solution) 931. A side aperture 930 communicates with the marker lumen 938 via fluid leak passages 935 formed in an MRI dark plug (e.g., collagen, nonferrous metal, plastic) 933 otherwise blocking the marker lumen 938.

In FIGS. 26-37, further illustrative versions of the shape of a sleeve and obturator are depicted that advantageously enhance the ability to locate suspicious lesions and to confirm proper placement of the side aperture thereof prior to taking biopsy samples by presenting a closed shape during penetration that may be changed to a shape that corresponds to a relieved area where samples will be taken, this shape visibly solid so as to be readily recognizable even when viewed from various angles of imaging slices.

This feature addresses drawbacks from relying upon the probe for imaging. Having a metallic substance in the imaging field may cause an artifact (local blooming) that may obscure the tissue of interest, such as attempting to use the biopsy probe itself to obturate the sleeve. Removing the probe during imaging and relying upon only the sleeve allows another imaging challenge to occur as an imaging slice through the hollow sleeve 22 may pose difficulties in identifying the side aperture. Often, the MRI compatible material selected gives no MRI return image, just as an air-filled void present across a side aperture thus presenting no return.

In FIGS. 26-27, an MRI compatible biopsy system 1210 includes a sleeve 1222 having a notch 1202 that corresponds to the location and size of the probe side aperture of the probe of the MRI biopsy device (not shown in FIG. 26). Moreover, the depth of the notch 1202 may be deeper than the probe side aperture in some instances to accentuate this location on the sleeve 1222 for imaging purposes.

An obturator 1224, shown in phantom in FIG. 26 in its "closed position" substantially blocking the notch 1202 of the sleeve 1222, may be advantageously formed of a thermoplastic as described with a distally presented ceramic bladed portion 1220 that extends through an open distal end 1221 of the sleeve 1222. Ceramic materials perform well in an M environment and hold a sharpened edge. With the notch 1202 closed by the co-axially inserted obturator 1224, the sleeve 1222 may be inserted into breast tissue.

In FIGS. 28-29, the obturator 1224 depicted advantageously includes a longitudinally bifurcated design as shown in FIGS. 28-29 wherein the lower portion 1223 includes a dovetail channel 1225 down its length that slidingly engages a dovetail tab 1227 extending down from an upper portion 1229 of the obturator 1224. The ceramic bladed portion 1220 is attached only to the lower portion 1223. As shown in FIG. 28, the upper portion 1229 may be proximally moved with the lower portion 1223 fully distally inserted into the sleeve 1222 to thereby open the notch 1202 of the sleeve 1222. Since the obturator 1224 is solid, during the 3-4 mm image slices taken by the MRI machine, the lower portion 1223 of the obturator 1222 fills in the notch 1202 so that its location may be readily ascertained. This two-piece obturator 1224 advantageously accommodates sleeve lumens with complex cross sectional shapes, such as the depicted oval-shaped sleeve 1222 (FIG. 27).

In FIGS. 30-31, a sleeve 1322 includes an integral sharp 1320 distally attached to its shaft 1319 that defines a circular cutter lumen 1321 and an underlying vacuum lumen 1323 (FIG. 31). In FIGS. 32-33, a round obturator 1324 is generally rod-shaped for insertion into the cutter lumen 1321 but with a notch recess 1325 formed corresponding to a notch 1302 of the sleeve 1322 (FIG. 30). Insofar as the round obturator 1324 is rotatable within the cutter lumen 1323, the notch recess 1325 may be selectively presented to open the notch 1302 in the sleeve 1322 or rotate about half a revolution to close the notch 1302.

The resulting effect in an MRI image scan is illustrated in FIGS. 34-35 wherein selectively closing the notch 1302 in the sleeve 1322 with the obturator 1324 presents a solid image but with little indication of where the notch 1302 is oriented. In FIGS. 36-37, with the obturator 1324 rotated to open the notch 1302, it is readily apparent where the notch 1302 is oriented.

Figure 39:
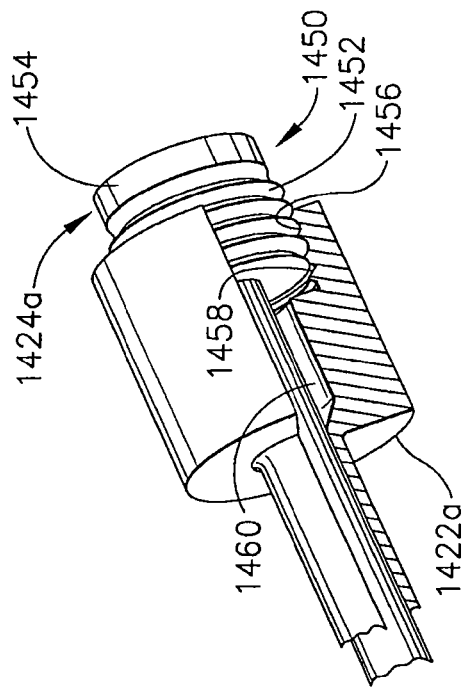
FIG. 39 is a perspective view of proximal ends of an obturator and sleeve, partially cut away to show a threaded connection for the MRI compatible biopsy system of FIG. 1.
Figure 38:
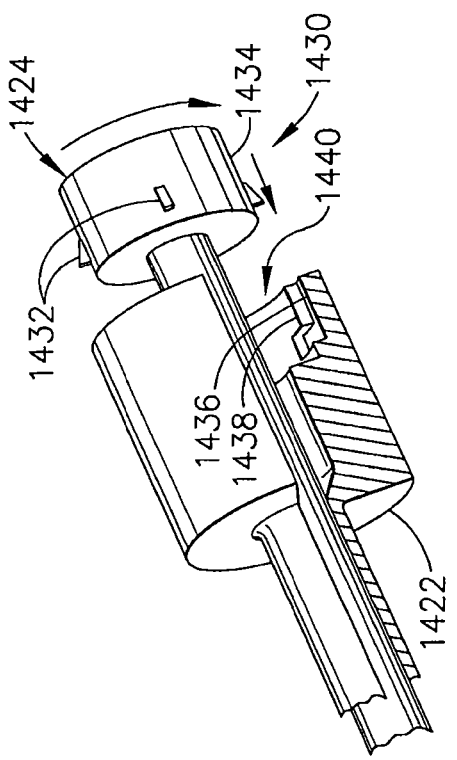
FIG. 38 is a perspective view of proximal ends of an obturator and sleeve, partially cut away to show a bayonet-style attachment for the MRI compatible biopsy system of FIG. 1.
Figure 40:
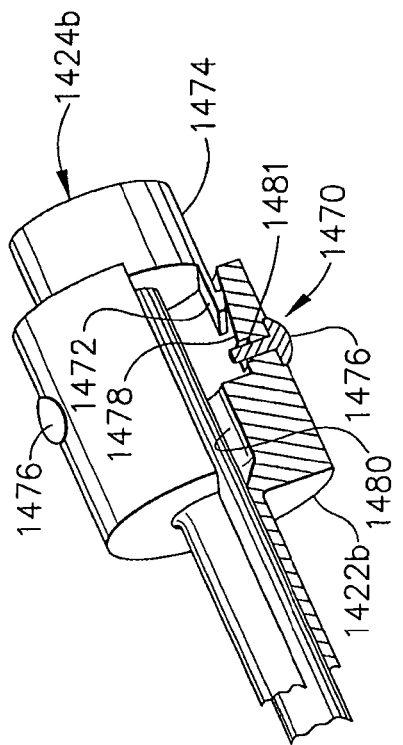
FIG. 40 is a perspective view of proximal ends of an obturator and sleeve, partially cut away to show a button release for the MRI compatible biopsy system of FIG. 1.

As an alternative to a latch locking feature between an obturator 1424 and a sleeve 1422, as described above for FIGS. 4-5, in FIG. 38, the obturator 1424 may selectively proximally attach to the sleeve 1422 to prevent inadvertent retraction and to assist maintaining a pneumatic/fluid seal with a bayonet-style attachment 1430 formed by cleats 1432 radially projecting from a cylindrical base 1434 of the obturator 1424 that is received within L-shaped recesses 1436 registered within a proximal bore 1438 of a sleeve lumen 1440 of the sleeve 1422. In FIG. 39, a threaded attachment 1450 is formed by male threads 1452 about a cylindrical base 1454 of an obturator 1424a that is threadingly received by female threads 1456 about a proximal bore 1458 of a sleeve lumen 1460 of a sleeve 1422a. In FIG. 40, a button release attachment 1470 is formed by locking hooks 1472 radially exposed about a cylindrical base 1474 of an obturator 1424b that are asserted into a proximal bore 178 of a sleeve lumen 1480 of a sleeve 1422b. The locking hooks 1472 engage a ramped recess 1481 in the proximal bore 1478, holding the obturator 1422b in its distal longitudinal position. For each locking hook 1472, a respective one of a pair of buttons 1476 extends through a respective ramped recess 1481, initially forced outward upon insertion of the locking hooks 1472. A user may depress the buttons 1476 while exerting a proximal pressure on the obturator 1424b to disengage the locking hooks 1472.

Additional therapeutic and diagnostic abilities are provided by use of a sleeve that is separate and apart, but is used in conjunction with an MRI biopsy device. This utility is enhanced by incorporating fluid and pneumatic seals within the sleeve so that bodily fluids may be selectively drained, anaesthesia or other medical compounds may be inserted into the surgical site of the biopsy, insufflation or deflation of the surgical site may occur, and/or vacuum assist of the MRI compatible biopsy system may be maintained.

Figure 41:
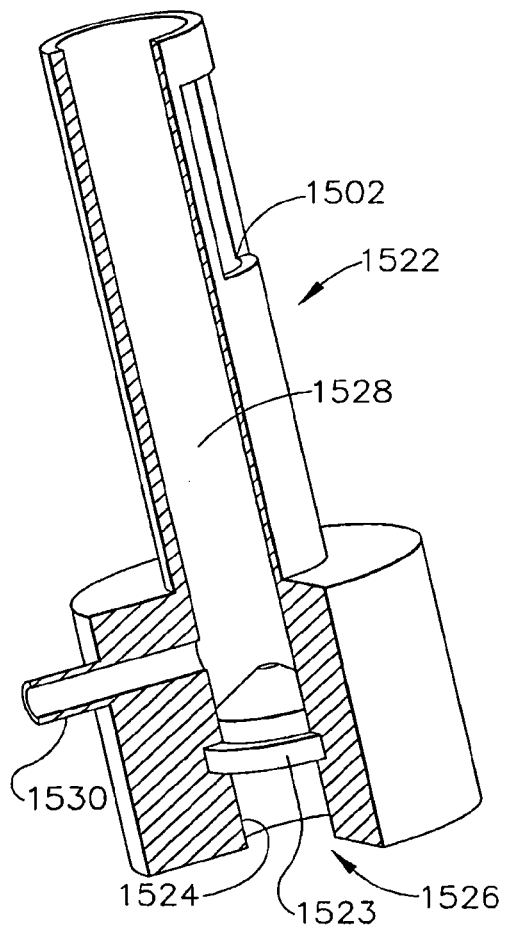
FIG. 41 is a perspective view of a sleeve partially cut away to expose a single port in its base, distal to a septum or full diameter seal.
Figure 42:
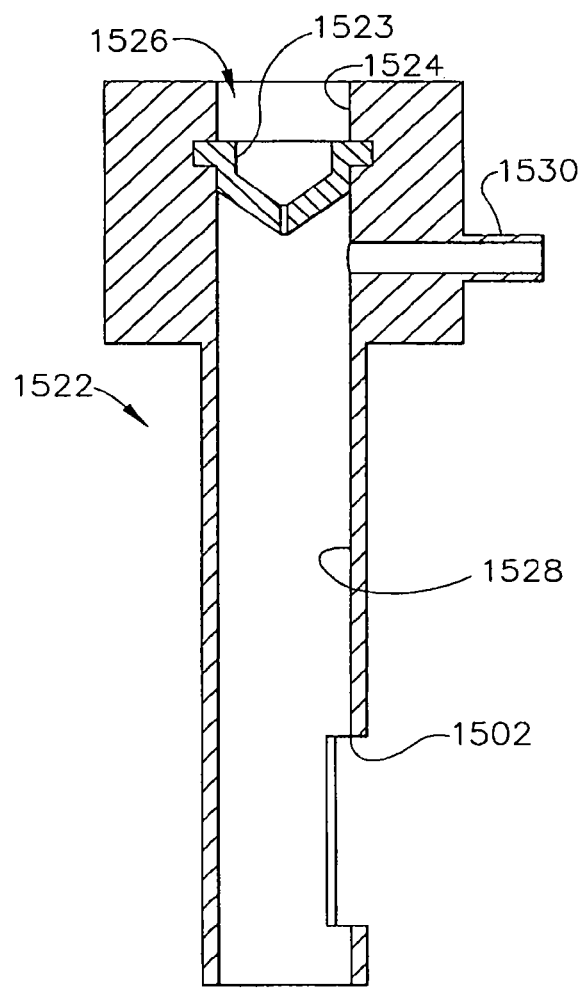
FIG. 42 is a cross section view along the longitudinal axis of the sleeve of FIG. 41.

In FIGS. 41-42, a sleeve 1522 incorporates a full-diameter seal, or septum 1523, across a proximal bore opening 1524 to a sleeve lumen 1526. Thereby, without an obturator, stylet or probe of an MRI biopsy device inserted coaxially in the sleeve 1522, a degree of pneumatic pressure (e.g., insufflation) may be maintained in the breast tissue and/or leaks of fluid prevented. The sleeve 1522 advantageously incorporates a port 1530 in its base that communicates with a distal portion 1528 of the sleeve lumen 1526 to a side aperture 1502 for purposes such as draining fluids or adding anaesthesia.

Figure 43:
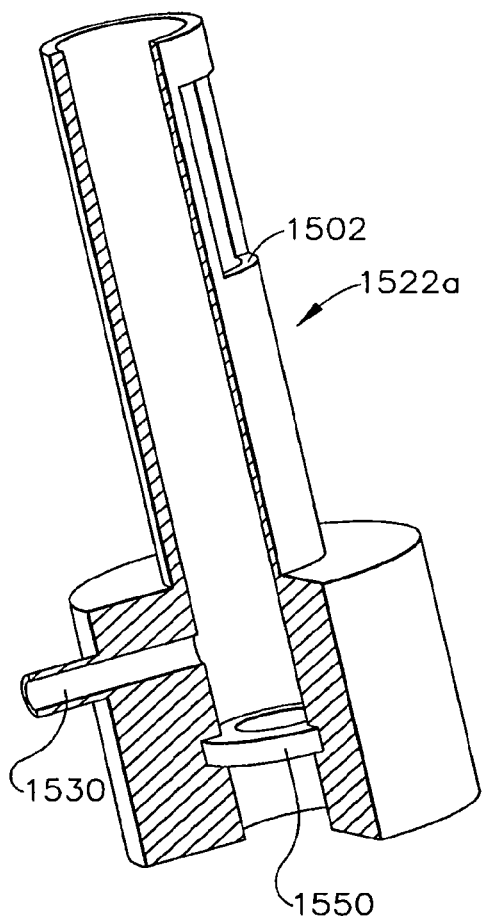
FIG. 43 is a perspective view of a sleeve, partially cut away to expose a single port in its base, distal to an O-ring dynamic seal.
Figure 44:
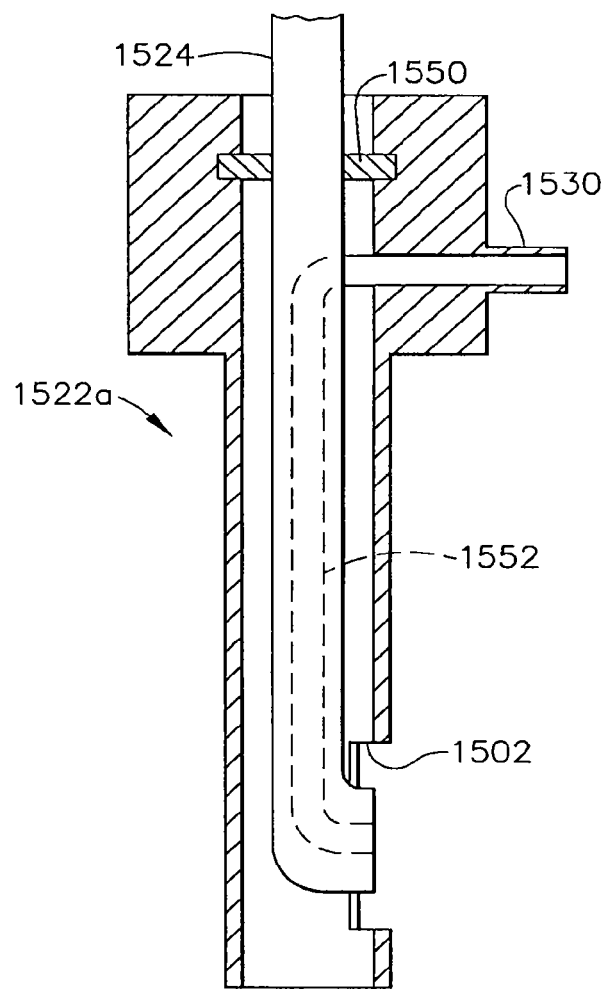
FIG. 44 is a cross section view along the longitudinal axis of the sleeve of FIG. 43.

In FIGS. 43-44, a similar sleeve 1522a incorporates an O-ring dynamic seal 1550 instead of the full-diameter seal that forms a seal with an obturator 1524, which may advantageously include a groove or passage 1552 down its length to allow fluid communication between the port 1530 and side aperture 1502.

In FIGS. 45-46, a similar sleeve 1522b incorporates a more distal O-ring dynamic seal 1560 and port 1562 to the proximal O-ring dynamic seal 1550 and proximal port 1530. An obturator 1524b may advantageously have two grooves or passages 1570, 1572 that communicate between a respective port 1530, 1562 and a respective side aperture 1502 and open distal end 1574.

With reference to FIG. 47, an obturator 1600 includes a sharp piercing tip 1602 that is advantageously shielded when not being employed to pierce tissue by a cylindrical sheath 1604. Thereby, the hazard of inadvertent injury and equipment damage is mitigated. In FIG. 48, as the obturator 1600 is inserted through a sleeve 1606, the cylindrical sheath 1604 passes through a seal retainer 1608 and is captured within a duckbill seal 1610 held between the seal retainer 1608 and a sleeve hub 1612. The piercing tip 1602 passes on through the sleeve hub 1612 and on through a cannula 1614 of the sleeve 1606. It should be appreciated that upon retraction of the obturator 1600, the piercing tip 1606 passes into the sheath 1604 and draws the sheath 1604 out of the sleeve hub 1612.

In FIGS. 49, 49A, an alternate obturator 1630 has a sharp piercing tip 1632 selectively shielded by a sheath 1634 that may be stowed proximally in a cylindrical relieved area 1636 so that the sheath 1634 conforms to an outer diameter of a shaft 1638 of the obturator 1630. A proximal control (not shown) actuates the sheath 1634 distally, either while inside of a sleeve 1640 as depicted or when the obturator 1630 is removed therefrom. The piercing tip 1632 is depicted as including a flat cutting blade 1642 that, at its base, extends the full diameter of the obturator shaft 1638. Thus, a distal portion 1644 of the sheath 1634 is split to pass on either side of the flat cutting blade 1642 (FIG. 49A).

The sleeve may be formed advantageously of a polymeric material, either homogenous or a composite, that is strong yet with thin walls so that the overall outer diameter need not be significantly larger than known biopsy probes, thereby being minimally invasive. The strength and small cross sectional area minimizes the size of the opening through the skin and thus typically avoids the need for sutures to close, reduces the force required to insert the probe, and minimizes trauma to breast tissue penetrated enroute to a suspicious lesion. The strength and rigidity advantageously maintain an open lumen for subsequent biopsy and other procedures therethrough. In addition, the sleeve is advantageously formed from materials that are biologically compatible to the patient and MRI compatible. Generally, the material thus does not create significant imaging artifacts that would obscure tissue images proximate to the sleeve 22.

Examples of polymeric materials that may be used, although not an all inclusive list, include polyimide, polyetherimides (e.g., ULTEM® resin by GE PLASTICS), thermoplastic liquid crystal polymers (LCP) (e.g., VECTRA® by CELANESE AG), polyethylether ketones (e.g., PEEK™ by VITREX), polyamide, polycarbonate (e.g., MAKROLON by BAYER POLYMERS), polysulfone, polyethersulfone, polyphenylsulfone (e.g., RADEL® by ROWLAND TECHNOLOGIES), and nylon and nylon copolymers.

In FIGS. 50-54, an obturator 1660 with a piercing tip 1662 has a protective sheath 1664 drawn proximally by interference with a sleeve hub 1666 of a sleeve 1667 (FIG. 50). Inward guide ridges 1668 of a proximal portion of the sheath 1664 move along guide slots 1670 formed in a shaft 1672 of the obturator 1660. A distal portion of the sheath 1664 includes a plurality of radially spaced longitudinal slits 1674 to form a plurality of protective flaps 1676 (e.g., four flaps in FIG. 51 and three flaps in FIG. 52) that are biased to deflect toward the longitudinal centerline when not held out by the shaft 1672 (FIG. 53). The inward bias of the protective flaps 1676 may be imparted to the sheath 1664 formed of spring metal, molded polymer, shape memory alloy annealed in closed position, etc.

Figure 55:
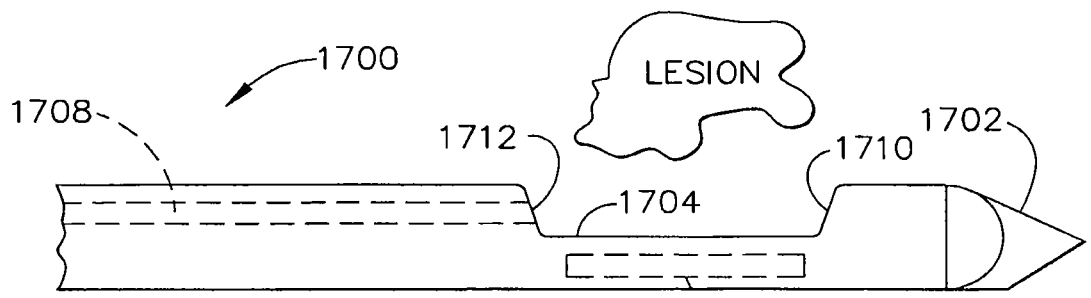
FIG. 55 is a right side view in elevation, taken in longitudinal cross section of a distal portion of an obturator having a lateral notch accentuated by an MRI visible marker and communicating with a marker deployment lumen.

In FIG. 55, a piercing member (e.g., probe, multi-function obturator) 1700 has piercing tip 1702 as described below with regard to FIGS. 77-80B. A lateral notch 1704 is accentuated by an underlying MRI visible marker 1706 and communicates with a lumen 1708 that may be used for aspiration, hemostasis, introduction of anesthesia or pharmacological compound, and/or a marking material. Leading and trailing edges 1710, 1712 of the lateral notch 1704 are rounded so as to avoid trauma to tissue during insertion and retraction.

Figure 56:
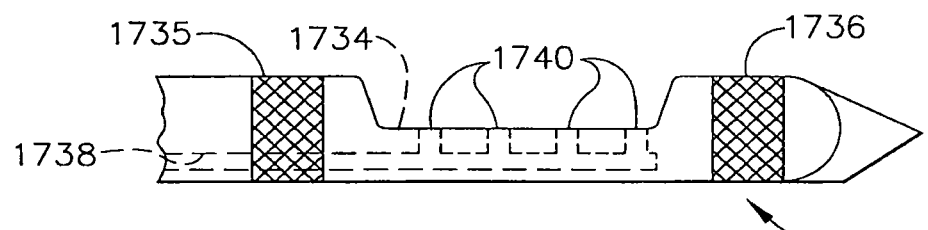
FIG. 56 is a right side view in elevation, taken in longitudinal cross section of a distal portion of an obturator having a lateral notch accentuated by flanking marker bands and communicating with an underlying vacuum lumen.

In FIG. 56, an alternate piercing member 1730 has a pair of MRI visible markers 1735, 1736 that flank a lateral notch 1734 with a lower lumen 1738 aligned to terminate below the lateral notch 1734 and to communicate thereto via holes 1740. Thereby, imagability and fluid introduction/extraction is facilitated by the piercing member 1730.

Figure 57:
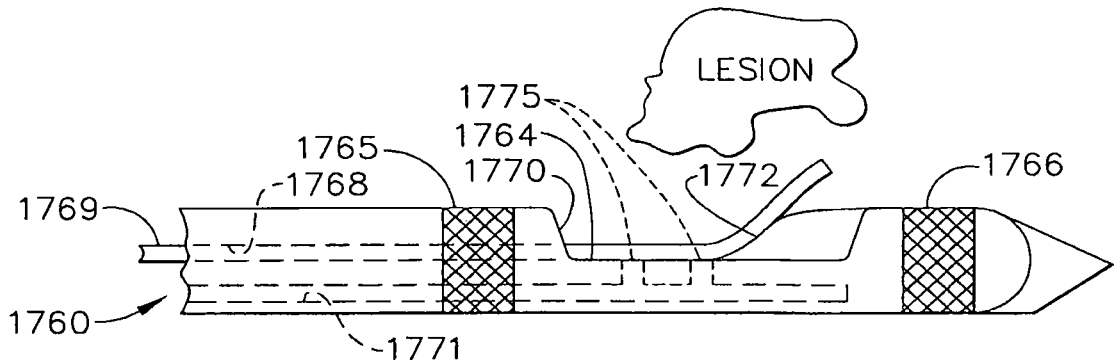
FIG. 57 is a right side view in elevation, taken in longitudinal cross section of an obturator with a side notch with a deployment ramp and marker/tool lumen.

In FIG. 57, a combination of the features of FIGS. 55-56 is shown with a further alternate piercing member 1760 having a pair of MRI visible markers 1765, 1766 that flank a lateral notch 1764. A marker lumen 1768 is aligned to enter a trailing edge 1770 of the lateral notch 1764 with a leading edge 1772 of the lateral notch 1764 ramped to eject a tool such as an inserted marker deployment tool 1769. A lower lumen 1771 terminates below the lateral notch 1764 and communicates thereto via holes 1775 for insufflation during marker deployment or for transferal of fluids.

Figure 58:
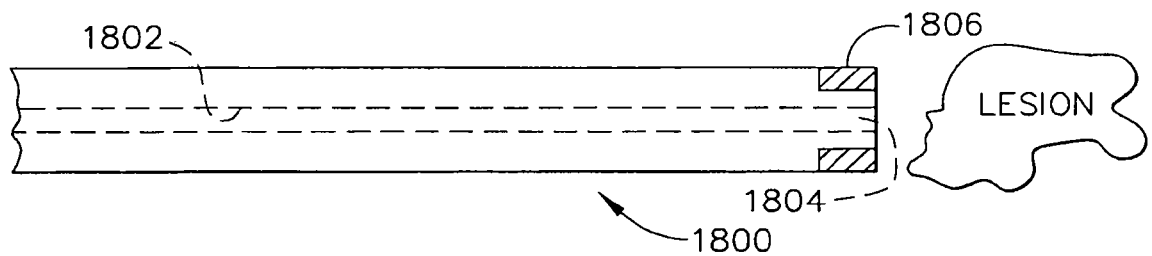
FIG. 58 is a right side view in elevation, taken in longitudinal cross section of a core needle having an annular ring MRI visible marker about an open distal end that communicates with a longitudinal marker/tool lumen.

In FIG. 58, a core needle 1800 having a lumen 1802 aligned to a longitudinal centerline thereof communicates to an open distal end 1804 for deploying core biopsy tools, a marker tool, wire for localization, an ablation device, etc. An imagable marker 1806 advantageously surrounds the open distal end 1804 to assist in proper placement of the core needle 1800.

Figure 59:
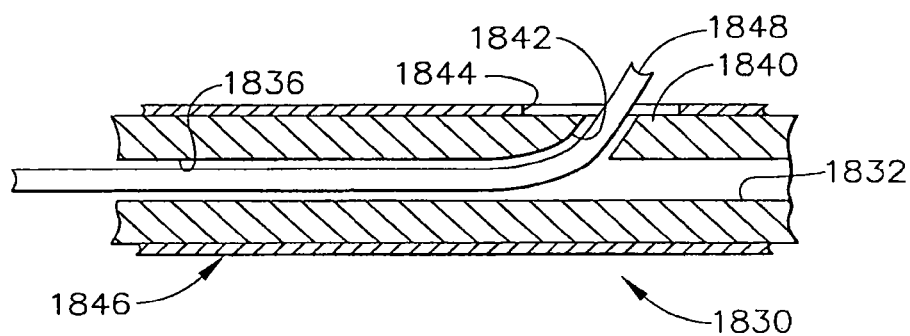
FIG. 59 is a right side view in elevation, taken in longitudinal cross section of a sleeve with a distal opening and a side aperture that selectively communicates with a longitudinal lumen with an adapter positioned in a first position.
Figure 60:
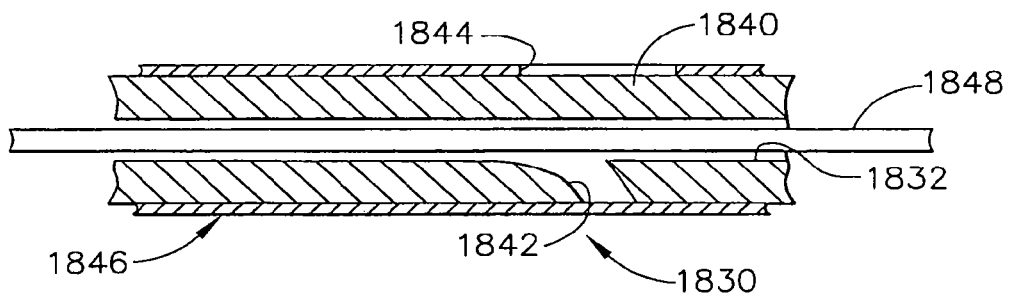
FIG. 60 is a right side view in elevation, taken in longitudinal cross section of the sleeve of FIG. 59 with the adapter in a second position.

In FIG. 59, an obturator 1830 includes a distal opening 1832 and a side deployment opening 1842 that selectively communicates with a longitudinal lumen 1836 with an adapter sheath 1840 that aligns the side deployment opening 1842 with a side aperture 1844 in a sleeve 1846, directing deployment of a tool 1848 through the side aperture 1844. In FIG. 60, the adapter sheath 1840 is rotated to misalign the side deployment opening 1842 with the side aperture 1844 of the sleeve 1846, directing deployment of the tool 1848 through the distal opening 1832.

In FIG. 61, a curl-biased tool 1870 is shown rotated to upward a deflected tip 1872. The curl-biased tool 1870 is inserted into an obturator 1874 in FIG. 62 with the deflected tip 1872 aligned such the tool 1870 is allowed to pass through a lumen 1875 to a side deployment guide 1876 aligned with a lateral aperture 1878 in a sleeve 1880. In FIG. 63, the curl-biased tool 1870 is rotated a half rotation to orient the deflected tip 1872 downward. When inserted into the obturator 1874 in FIG. 64, the tool 1870 deploys out of a distal opening 1882.

Figure 65:
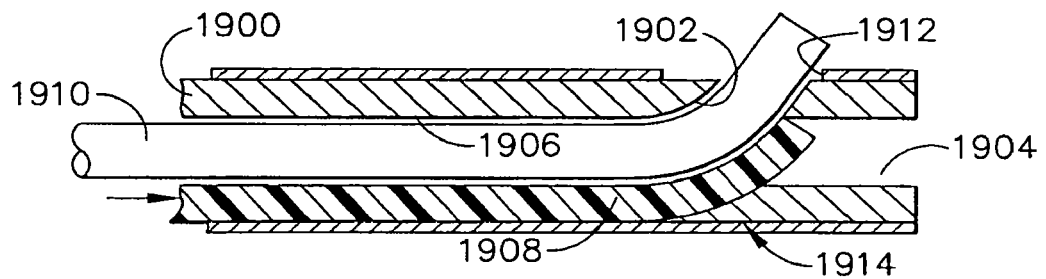
FIG. 65 is a right side view in elevation taken in longitudinal cross section of a sleeve having a push slide distally extended to direct a tool out a side aperture.
Figure 66:
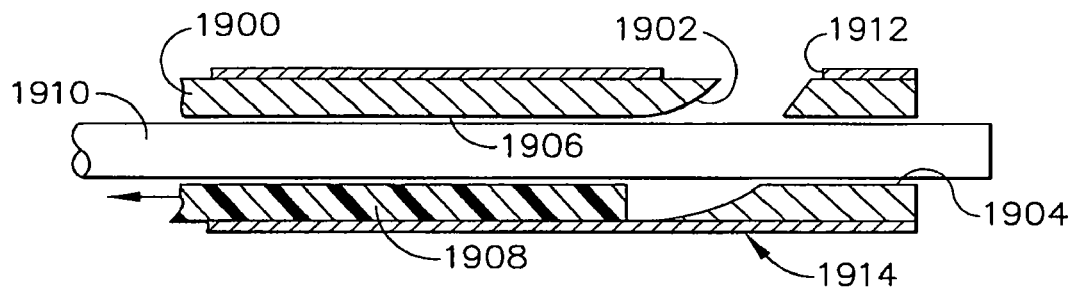
FIG. 66 is a right side view in elevation taken in longitudinal cross section of the sleeve of FIG. 65 having the push slide retracted to allow the tool to extend out of a distal opening.

In FIG. 65, an obturator 1900 includes a side opening 1902 and a distal opening 1904 of a lumen 1906. A distally-moving diverting member 1908 is ramped across the lumen 1906, aligned to guide a tool 1910 toward the side opening 1902, and thus extending out a lateral aperture 1912 of an encompassing sleeve 1914. Retracting the diverting member 1908 in FIG. 66 opens up the lumen 1906, allowing the tool 1910 to extend out of the distal opening 1904.

Figure 67:
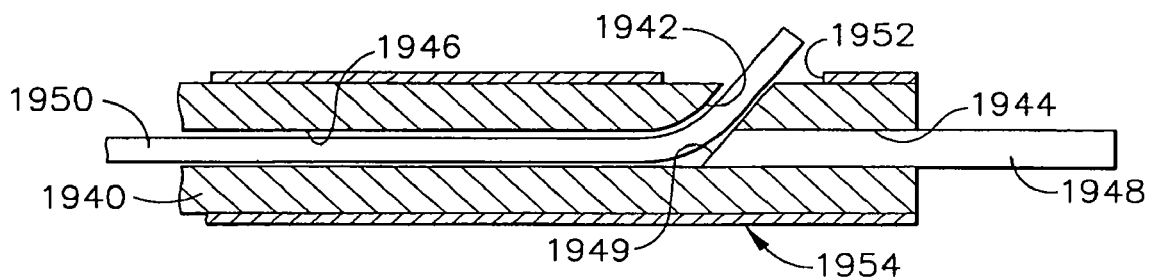
FIG. 67 is a right side view in elevation taken in longitudinal cross section of the sleeve of FIG. 62 with a plug inserted into the distal end to divert a tool out the side aperture.

In FIG. 67, an obturator 1940 includes a side opening 1942 and a distal opening 1944 of a lumen 1946. A plug 1948 may be inserted into the distal opening 1944, configured such that a proximal end 1949 is ramped and aligned with the side opening 1942 to guide a tool 1950 toward the side opening 1942, and thus extending out a lateral aperture 1952 of an encompassing sleeve 1954. Removing the plug 1948 (not shown) opens up the lumen 1946, allowing the tool 1950 to extend out of the distal opening 1944.

Figure 68:
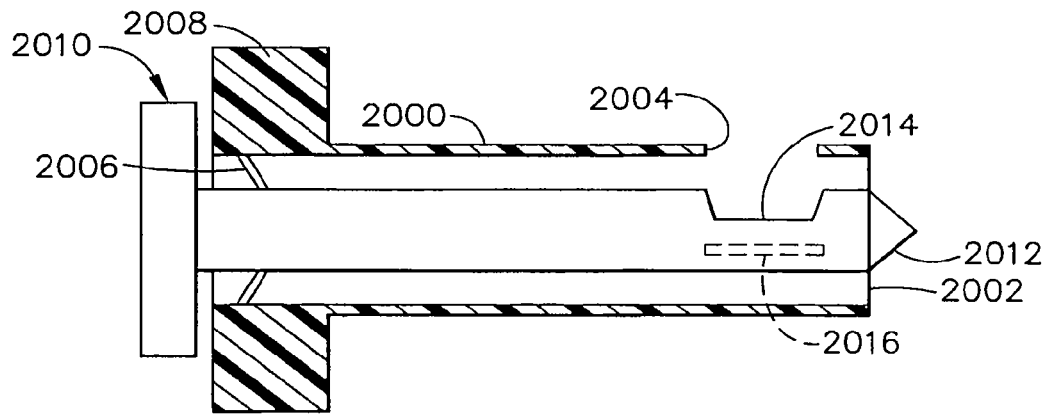
FIG. 68 is a right side view in elevation taken in longitudinal cross section of a sleeve with an open distal end pneumatically sealed to a an obturator with an imagable side notch with an underlying MRI bright marker.
Figure 69:
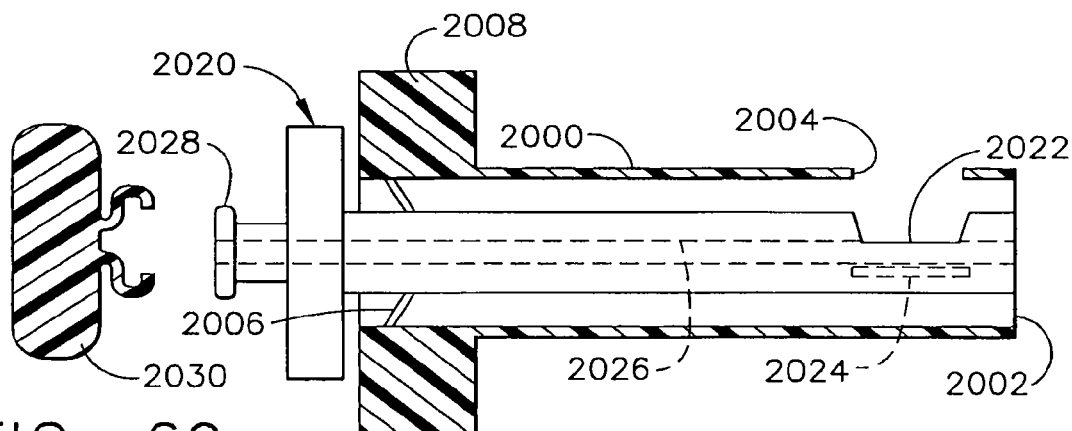
FIG. 69 is a right side view in elevation taken in longitudinal cross section of the sleeve of FIG. 68 pneumatically sealed to a marker stylet with a side aperture accentuated by an underlying MRI bright marker and communicating with a marker/tool lumen proximally sealable by leur fitting a coupled cap/handle.
Figure 70:
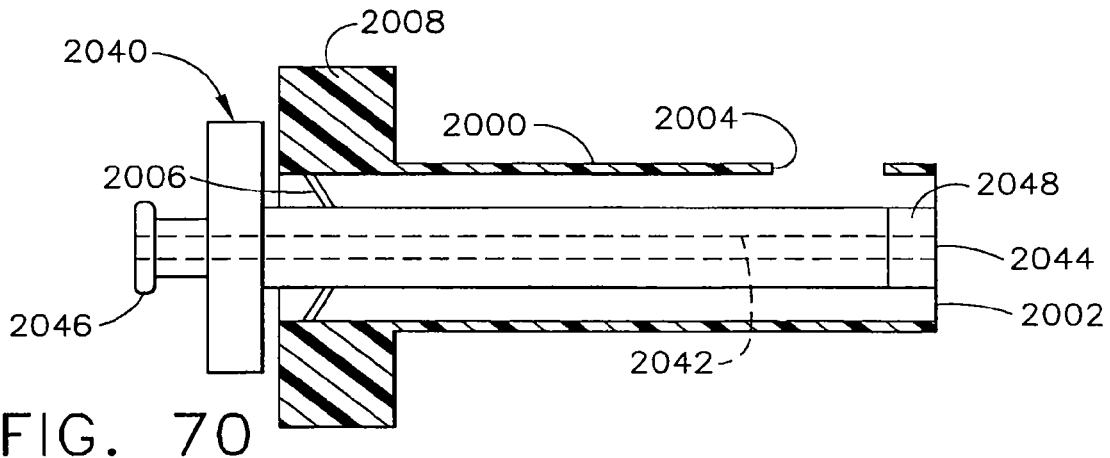
FIG. 70 is a right side view in elevation taken in longitudinal cross section through the sleeve of FIG. 68 with a core needle stylet pneumatically sealed therein.

In FIGS. 68-70, a sleeve 2000 with an open distal end 2002, a side aperture 2004, and a proximal septum or seal 2006 encompassed by a sleeve hub 2008 is shown. In FIG. 68, during penetration and guidance/confirmation imaging, an obturator 2010 is inserted into the sleeve 2000 with a seal formed therebetween by the seal 2006. The obturator 2010 provides a penetrating tip 2012 and an imagable side notch 2014 accentuated with an underlying marker 2016. In FIG. 69, a marker stylet 2020 is inserted into the sleeve 2000 and sealed therein. The marker stylet 2020 includes a side notch 2022 accentuated by an underlying marker 2024 that communicates with a lumen 2026 that proximally terminates in a leur fitting 2028, selectively sealed by a handle cap 2030 or attached to various pneumatic or fluid handling connections. In FIG. 70, a wire localizer/core needle stylet 2040 is inserted into the sleeve 2000 and sealed therein. A lumen 2042 communicates between a distal opening 2044 and a proximal leur fitting 2046. A marker ring 2048 about the distal opening 2044 assists in confirmation imaging.

Figure 71:
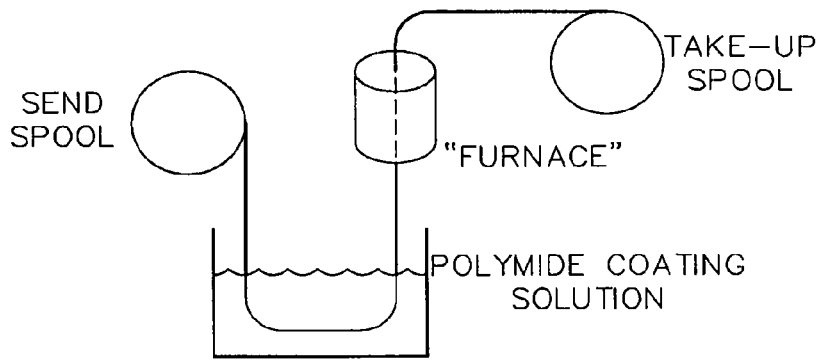
FIG. 71 is a diagrammatic view of a process to produce polymide for an MRI biopsy device.
Figure 72A:
Figure 72B:
Figure 72C:
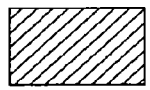
Figure 72D:
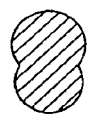

In FIG. 71, a polyimide process may be used to form this material wherein a film is formed from solution. A standard practice is to coat continuous wire by passing wire from a spool, through a polyimide coating solution through a furnace to a take-up spool. The wire usually goes through multiple processes to build up the coating thickness. The inline furnace or heating element drives off the solvent and causes partial cross-linking of the polyimide. Full cross-linking occurs usually when the desired coating thickness has been achieved. The full cross-linking temperature occurs at a much higher temperature than the temperature used during coating.

To create the free standing polyimide tube, the wire is then removed. For example, lengths of the coated wire may be cut with the wire pulled or drawn from both ends to stretch it, thereby reducing its outer diameter until separated from the coating, then withdrawing the wire. Alternatively, an easily chemical etched material may be used for the wire. For instance, a cooper wire may be dissolved by a persulfate complexing solution leaving behind a free standing polyimide tube.

Figure 73A:
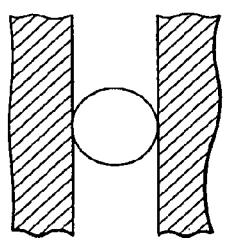
FIG. 73A is a front view of a perform sleeve placed within a compression fixture.
Figure 73B:
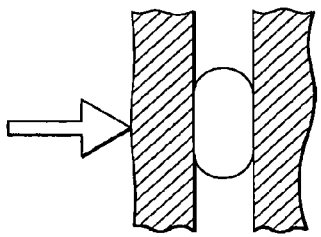
FIG. 73B is a front view of the sleeve of FIG. 73A after lateral compression to form an oval cross sectional shape.
Figure 73C:
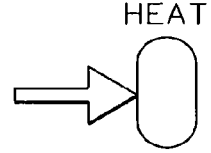
FIG. 73C is a front view of the oval sleeve of FIG. 73B after heating to form a cohesive permanent shape.

Further, to create more complex cross sectional shapes (FIG. 72A-72D) (e.g., oval, etc.) the polyimide tube may be placed in a form prior to a final cross-linking heat step. In addition, a mandrel may be inserted through the polyimide tube to further define the shape, especially in cooperation with compressing outer forms, such as depicted in a sequence of FIGS. 73A-73C for an oval and in a sequence of FIGS. 74A-74E for a waisted oval.

Figure 76A:
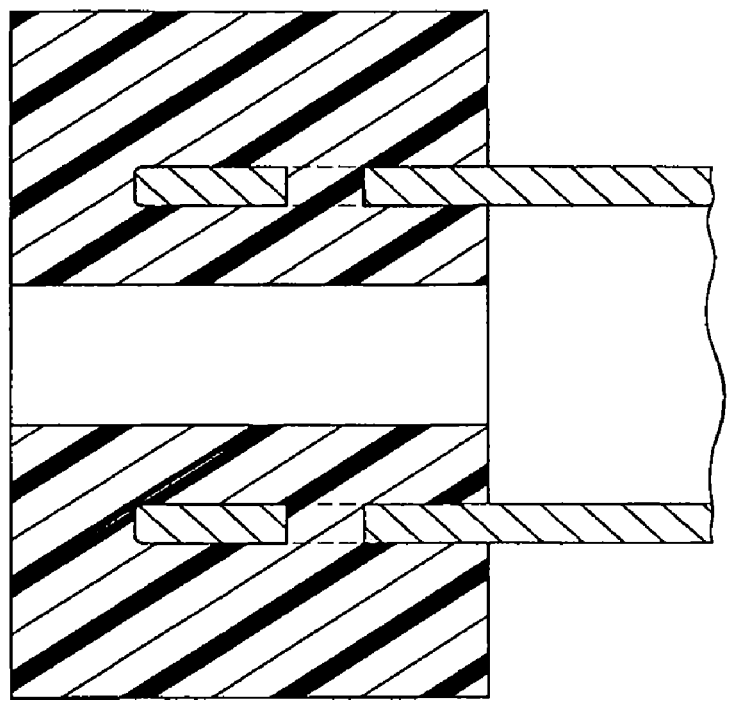
FIG. 76A is a right side view in elevation through a longitudinal cross section of a proximal portion of a sleeve having laser formed through holes over molded with a sleeve hub.
Figure 76B:
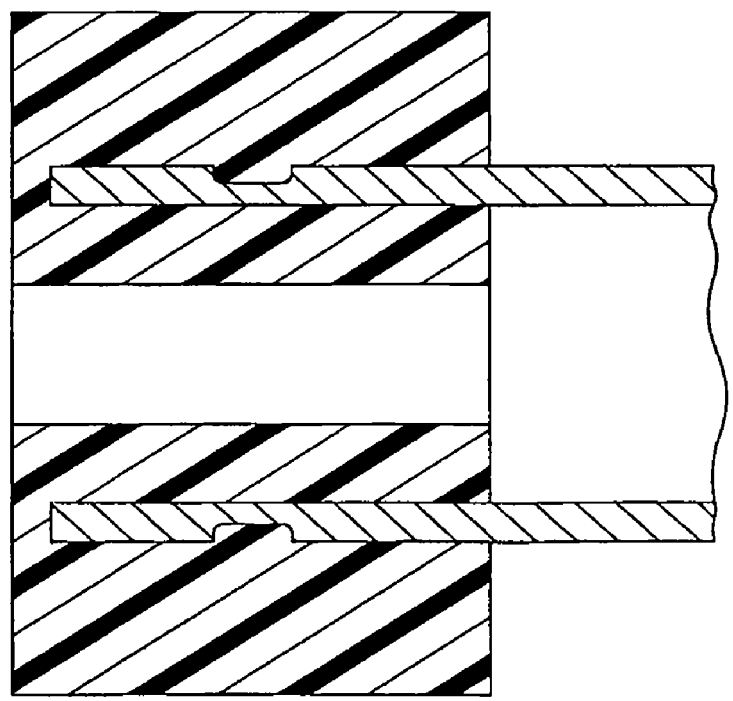
FIG. 76B is a right side view in elevation through a longitudinal cross section of a proximal portion of a sleeve having a laser formed relieved area over molded to form a sleeve hub.

In FIGS. 75, 76A-76B, follow-on processes to create a side aperture at its distal end and/or mounting holes at its proximal end may then be formed. For instance, laser cutting by an eximer or YAG laser may form desired perforations. Further, an eximer laser may not be used to form through holes but also reliefs sufficient to create enough mechanical interference with over-molded parts to ensure assembly integrity during normal loading and tension. Full perforations may be used to allow an over-molded part, such as proximal end mounting mechanisms, to flow through the holes before hardening.

To achieve holes in the tube of FIG. 75, several methods may be employed. For instance, an eximer or YAG laser machine may create the perforations (FIG. 76A). The eximer laser may also be programmed to create not only through holes, but also reliefs. Reliefs may be substituted to create sufficient mechanical interference with an overmolded part to ensure assembly integrity during normal loading and tension (FIG. 76B). As another example, a punch or die-cut process may be integrated into the forming mold. The parts may be cut, trimmed and punched followed by heat treatment in the same form.

The forming molds advantageously should be both hard and have high thermal conductivity. Steel, while hard, has low thermal conductivity. Copper and brass, by contrast, have high thermal conductivity, but are softer. An alloy of hardened aluminum may be a suitable material for the forming molds with steel inserts for punching holes.

A sheath may also be formed from a braided composite. Individual fibers of the braid may be wound on an initial layer of polyimide and then sealed in a layer of polyimide. The braid may be of an MRI compatible ceramic fiber, such as NEXTEL by 3M.

Portions of the sleeve and/or obturator may be formed from materials chosen for their imagability, either dark or bright. Under most standard MRI scan sequences used to image breast tissue for possible cancer, known engineering plastics appear dark or have low contrast, which may cause problems when identifying such components for localizing and diagnostic purposes. Consequently, in addition to considerations described above when forming a sleeve of sufficient strength and MRI compatibility, it may be advantageous to substitute or augment material that is bright to an MRI machine but that does not create a significant artifact. In addition or as an alternative, an overmold or coat or insert material that appears bright to an MRI machine may be formed over structural "dark" material. In addition or as an additional alternative, a "dark" material chosen for strength or other reasons may be overmolded or coated or inserted with materials that absorb a contrast enhanced or bright fluid. In addition or as yet another alternative, a composite or multilayered material may be formed with some layers chosen for properties such as strength and others chosen for their characteristic of being visible to the MRI machine.

Particular patterns of marker bands, for instance, may be placed inferior to the side aperture of the sleeve, or in spaced rings proximal to or distal to the side aperture about the sleeve. As an example, $Dy_2O_3$ or $Fe_2O_3$ may be mixed with an ink and then printed onto portions of the sleeve 22 or used to fill recessed grooves on the obturator 24 or stylet. Such patterns may also be created by dispersing $Dy_2O_3$ or $Fe_2O_3$ as filler into a thermoplastic so that isit may be applied to the sleeve 24 and/or obturator by reflow or thermal bonding. Yet another approach is to insert mold $Dy_2O_3$ or $FC_2O_3$ into the device, such as by loading a molded/extruded component plastic (e.g., PEEK, ULTEM) and attach (e.g., over mold a ring of 30% $Dy_2O_3$ in PEEK).

As yet a further alternative, regions of material may be capable of being infused or hydrated with a water based solution and/or a contrast agent (e.g., gadolinium chelate) that would thus appear bright when imaged. As yet another alternative, regions of material, such as infusion or hydration, may occur immediately before use or such material may be pre-hydrated and aseptically packaged.

In particular, certain polymers that appear bright to an MRI machine may be selected to include synthetic water soluble polymers that have high alcohol or carboxilic acid functionality. For example, cellulose derivatives include carboxymethyl cellulose, ethyl cellulose, hydroxyethyl cellulose, carboxymethyl hydroxyethyl cellulose, ethylhydroxyethyl cellulose, and methyl cellulose. As another example, acrylates include polyacrylic acid salts and polyacrylamide. For yet another example, other artificial materials include polyvinyl alcohol (PVA), polyvinyl methyl ether, polyvinylpyrrolidone (PVP), and poly(ethylene) oxide (PEO). As yet a further example, natural products and derivatives include cornstarch, gelatin, dextrins, alginates, casien, collagen (e.g., bovine, etc.) and natural gums (e.g., xanthum, tragacanth, karaya, etc.). As yet an additional example, biopolymers include polylactic acid, di-lactide-co-glycolide (PLG) (i.e., as an example of lactide isomers (D, L, DL) (MP=225-230° C.)), polycaprolactone (MP=60° C.), lactates and gluconates, polydioxanone, polyglactin (i.e., suture materials).

Other polymers that appear bright to an MRI machine include silicone based materials such as siloxanes functionalized with hydroxyl (—OH) groups and carboxylic acid groups and such as silicones (i.e., both fluid and gum rubbers).

In an illustrative version when making polymeric materials image without excessive artifact in MRI, dysprosium oxide ($Dy_2O_3$) or hermatite ($Fe_2O_3$) was dispersed as a filler in a thermoplastic carrier that can be thermoformed (e.g., extruded, molded, etc.). A marker thus formed, when integrated into a device such as the sleeve 22 or obturator 24, improves device visibility under MRI (e.g., gradient echo EPI, flash, real-time true FISP). In particular, $Dy_2O_3$ (35%) was dispersed in Rilsan® Polyamides (75%) ATOFINA Chemicals, Inc. This combination was extruded into thin-walled (i.e., 0.002 inch) tubing, which was quite visible using Flash. Further, Flash appears to create the best visibility for susceptibility devices (includes $Dy_2O_3$ and $Fe_2O_3$), EPI was less visible, and real-time true FISP was not visible.

Other polymers that appear bright to an MRI machine include hydrophilic polymer and polymeric foams such as urethane foams that rapidly absorb moisture when adding hydrophilic block-copolymer segments are added into the urethane backbone or use surface functionalization such as that effected by plasma oxidation or chemical oxidation. Similarly, other polymers may be foamed such as starch with linear low density polyethylene, expanded polytetrafluoroethylene (PTFE), or other materials (e.g., polyimides, polyolefins, polystyrenes, polyesters, nylons, acrylics, acrylates, polycarbonates, melamines, polyvinylchloride, polyvinylacetate).

As implementations wherein aqueous based solutions are infused or hydrated into such materials, such solutions include gadolinium based compounds for T1 enhancement in solution including diethylene triamenepentaacetic acid (DTPA), gadoteridol (GD-HP-D03A) (nonionic), gadodiamide (GD-DTPA-BMA) (nonionic), and GdDOTA (ionic). Such solutions also include iron-based solutions for T2 enhancement such as Feridex (super paramagnetic agent).

Accentuating the side aperture 102 of the sleeve 22 has been discussed above as in the choice of materials or shaping of the obturator that selectively closes the side aperture 102. It is also mentioned above that specific regions of the sleeve 22 may be accentuated. With regard to the latter, marking the side aperture 102 with material that is bright under MRI imaging may be accomplished with commercially available contrast agents to leverage existing capital equipment and supply channels. Examples of such contrast agents are gadolinium ($Gd^{+3}$) (e.g., MAGNEVIST® (gadopentetate dimeglumine) by BERLEX); iron ($Fe^{+3}$) (e.g., FERIDEX IV® (ferumoxides injectable solution); and manganese ($Mn^{+2}$) MnDPDP (e.g., TESLASCAN™ Mangafodipir by AMER- SHAM HEALTH). A matrix of a polymer may swell in the presence of water to create a contained, hydrated environment for the contrast agent. These polymers would be permeable to water, but have limited permeability of the contrast agent molecules. The contrast agents may be chemically bound to the matrix to reduce or limit their migration out of the matrix. Examples of polymers suitable for such a matrix include hydrogels, urethane acrylates with hydrophilic blocks, latex paints/emulsions, coatings loaded with hydrophilic particulate such as silica particles and particle agglomerates.

A void within an obturator may include a vent and a septum. Contrast agent may be injected through the septum with air vented through the vent. Hydrophilic foam or cellulose material (e.g., cotton) within the void may be used to better retain the contrast agent. Alternatively, contrast chelate may be preloaded onto the hydrophilic foam or cellulose material and hydrated during the procedure.

As an alternative or an addition to materials that are bright under MRI, active marker band technologies may be incorporated to illuminate a side or distal aperture in the sleeve 22. Examples of active illumination used in different applications are described in U.S. Pat. Nos. 5,211,165; 5,307,808; 5,318,025; 5,437,277; 5,443,066; 5,445,150; 5,715,822; 5,882,305 and 6,289,233. Coils are formed proximate to the sampling aperture, such as side aperture 102 with electrical connections formed along the length of the sleeve 22. Polyimide is a particularly good material choice for forming a substrate for such coils and electrical connections because of significant development of technology and processes to form thin film electronic circuits on polyimide. Electrical isolation may be achieved with overcoats of another layer of polyimide. An inductive coil about the base of the sleeve 22 that is in electrical communication with these marker bands would allow RF coupling to these coals and provides RF isolation for the patient. Alternatively, a dedicated integrated circuit and power source (e.g., battery, capacitor) may be integrated into the sleeve 22 to eliminate the need for external excitation. These marker band coils may be in parallel or serial or separately excited. As another alternative, two coils may be serially arranged but with a center tap.

In some applications, it may be desirable to incorporate thermistors or thermocouples that may be monitored for an unacceptable temperature rise (e.g., 4° C.) for automatic shutdown. As a further alternative, optical converters may be incorporated into the sleeve so that light fibers may communicate a signal in and out.

Similar considerations are applicable to the piercing portion of the sleeve or obturator; however, the needs for piercing tissue may lead to other choices. As an introduction, metallic components used for MRI safe medical devices must be biocompatible and not interact with the strong magnetic fields used during MRI imaging. Standard 300 and 400 series stainless steels are ubiquitous in medical device design. These materials combine the features of corrosion resistance, biocompatibility, hardness and tensile properties. These materials are primarily ferrous. The 300 series materials have less interaction with magnetic fields than the 400 series materials, but have lower hardness properties, which limits their utility for sharp edges for cutting and/or penetrating tissue. All 300 and 400 series materials have significant concentrations of iron, which limits their utility for MRI imaging applications.

Iron Alloys: There is at least one ferrous, austenitic alloy, which remains non-magnetic even after severe forming operations, Super Alloy Nitronic. Other related materials include Carpenter 22Cr-13Ni-5Mn, HPA 50, XM-19. Alloy 316 is also relatively non-magnetic, but becomes more magnetic as it is work hardened. The alloy compositions are as follows:

TABLE 1

| | Steel Composition Range (%) | | |
|---|---|---|---|
| Element | Nitronic 50 | 316L | Ideal |
| Carbon | 0.06 max | 0.03 max | 0.06 max |
| Manganese | 4-6 | 2.0 | 2-6 |
| Phosphorus | 0.04 max | 0.045 max | 0.045 max |
| Sulfur | 0.03 max | 0.03 max | 0.03 max |
| Silicon | 1.0 max | 1.0 max | 1.0 max |
| Chromium | 20.5-23.5 | 16-18 | 16-24 |
| Nickel | 11.5-13.5 | 10-14 | 10-14 |
| Molybdenum | 1.5-3 | 2-3 | 1-3 |
| Copper | | | |
| Cobalt | 0.1-0.3 | | 0.3 max |
| Titanium | | | |
| Columbium | 0.1-0.3 | | 0.3 max |
| Aluminum | | | |
| Tantalum | | | |
| Vanadium | 0.1-0.3 | | 0.3 max |
| Tungsten | | | |
| Boron | | | |
| Nitrogen | 0.2-0.4 | | 0.4 max |
| Iron | Balance | Balance | Balance |

The ideal range is that range into which iron based alloys need to fall to have minimal magnetic properties.

Cobalt Alloys: Cobalt alloys are an excellent alternative. These alloys are hard and do not interact strongly with the magnetic fields. Examples of such alloys include L-605 and MP-35. Cobalt alloys are optimized for either wear resistance, high temperature use and/or corrosion resistance. For breast biopsy tools, the wear resistance and corrosion resistance properties are of greatest interest. The primary alloying element to provide these properties is the addition of chromium (U.S. Pat. No. 873,745). Molybdenum and tungsten are outstanding strengthening agents. The addition of carbon improves the wear resistance significantly. The addition of up to 2.4% carbon results in the formation of carbides. An example of this alloy is the trade name, Stellite. An alternate method for improving wear is the addition of the combination of molybdenum and silicon. An example of this alloy is the trade name Tribaloy. This alloy has been deposited successfully as a thin film.

The addition of nickel was found to improve the high temperature performance. An example of this alloy is Stellite 21 with approximately 2.5% nickel. Later alloys such as the X-40 and L-605 have increasing nickel content to around 10%. In general alloys with the following composition ranges are optimum for Co based, high tensile strength, high hardness materials:

TABLE 2

| | Composition Range (%) | | | |
|---|---|---|---|---|
| Element | L-605 | MP-35 | CCM | Ideal |
| Carbon | 0.05-0.15 | 0.025 max | 0.1 max | 2.4 max |
| Manganese | 1-2 | 0.15 max | 1 max | 0-2 |
| Phosphorus | 0.03 max | 0.015 max | | 0.2 max |
| Sulfur | 0.03 max | 0.01 max | | 0.05 max |
| Silicon | 0.4 max | 0.15 max | 1 max | 0-2 |
| Chromium | 19-21 | 19-21 | 26-30 | 19-35 |
| Nickel | 9-11 | 33-37 | 1 max | 0-40 |
| Molybdenum | | 9-11 | 5-7 | 0-15 |
| Copper | | | | 0-1 |
| Cobalt | Balance | Balance | | Balance |

TABLE 2-continued

| | Composition Range (%) | | | |
|---|---|---|---|---|
| Element | L-605 | MP-35 | CCM | Ideal |
| Titanium | | 1 max | | 0-2 |
| Columbium/Niobium | | | | 0-1 |
| Aluminum | | | | 0-1 |
| Columbium + Tantalum | | | | 0-1 |
| Vanadium | | | | 0-1 |
| Tungsten | 14-16 | | | 0-20 |
| Boron | | 0.01 | | 0-0.05 |
| Nitrogen | | | 0.25 max | 0.25 max |
| Iron | 3 max | 1 max | 0.75 max | 5 max |

Nickel Based Alloys: Nickel-Chromium-Molybdenum alloys are another approach to hard, non-magnetic metal alloys. Some members of this alloy class have greater than 5% iron (Inconel 600) and nickel based alloys even without iron can have significant magnetic properties. The composition and processing of the alloy is key to its magnetic and physical properties. Some alloys such as Inconel 625, have Rockwell hardness exceeding 95 Rb.

TABLE 3

| | Composition Range (%) | | | |
|---|---|---|---|---|
| Element | Inconel 600 | Inconel X750 | M252 | Ideal |
| Carbon | 0.08 | 0.1 | 0.1 | 2 max |
| Manganese | 0.5 | 1.0 | 1.0 | 0-2 |
| Phosphorus | | | | 0.2 max |
| Sulfur | | | | 0.05 max |
| Silicon | .25 | 0.5 | 0.7 | 0-2 |
| Chromium | 15.5 | 15. | 19 | 10-20 |
| Nickel | 76 | 72 | 53.5 | Balance |
| Molybdenum | | | 10 | 0-15 |
| Copper | 0.25 | | | 0-1 |
| Cobalt | | 1.0 | 10 | |
| Titanium | | 2.5 | 2.5 | 0-2 |
| Columbium/Niobium | | | | 0-1 |
| Aluminum | | 0.7 | 0.75 | 0-2 |
| Columbium + Tantalum | | | | 0-1 |
| Vanadium | | | | 0-1 |
| Tungsten | | | | 0-2 |
| Boron | | | | 0-0.05 |
| Nitrogen | | | | 0.25 max |
| Iron | 8 | 7 | 2 | 10 max |

Composite Approaches: Soft metals, such as titanium or fully annealed 316 SS have appropriate magnetic properties, but have poor hardness and thus poor cutting ability. These materials can be locally hardened at the cutting or penetrating surface by the follow processes: (1) Brazing, welding, or joining a hard material edge to the soft metal; (2) Vapor deposition (chemical, vacuum, etc) of a hard material such a titanium nitride; (3) Ion beam implantation; (4) Localized heat/work hardening via laser or frictional heating; (5) Or a combination of the above methods.

Non-Metallic Materials Options: Other non-metallic materials useful for creating sharp, cutting surfaces include the following amorphous/ceramic materials: (1) Alumina; (2) Zirconia (including yttria stabilized); (3) Silica. Single crystal materials include: (1) Silicon; (2) Germanium; (3) Carbon in the diamond form; (4) Aluminum in the sapphire form; (5) Ruby. The single crystal cutting edges may be created using the single crystal properties of the materials. Preferential etches, such as alcohol-KOH on 1,0,0 silicon wafers, can be used too pattern precise angles and thus sharp edges.

Penetrating Member Geometries: The blade geometry is important in the optimization of the force to penetrate tissue. The early pyramidal design on trocars has recently been superceded by flat blade designs. The theory of point and cutting angles date back to Augur bits in 1800's. Cutting theories have always been studied, developed and refined for wear issues, etc., in recent years. The key factor that governs this optimization is the geometry at the tip as torque and thrust force (the amount surgeon pushes the trocar) is fixed for a given diameter of blade. The majority (almost 90%) of penetration forces is controlled by the tip as it separates the layers of tissue. Using lower penetration forces is beneficial as this causes less pain. There is 120 degree motion of torque in both direction while inserting the blade. The thrust force with which the blade is pushed is not measured. An assumption may be made that the trocars are pushed at around 5 lbs. The cutting blade is the major element of the tip, which separates (cuts) the tissue. In the current design (FIG. 77) there is sharp cone angle of 30 to 35 degrees with a flat blade perpendicular to the surface. This invention explores to optimize the optimization of the tip design with offset cutting edges with a cutting angle and a secondary flat point angle at the center, as depicted in FIGS. 78A-78B.

Definitions: Dynamic cutting angle ($\alpha_{dyn}$): The angle measured in a plane through a point on the cutting edge and perpendicular to the horizontal line that passes that point and intercepts with the drill center axis, between the rake face and normal line of that plane which contains both the cutting edge and the cutting velocity vector. The cutting velocity vector is the vector sum of the rotary cutting velocity vector and feed velocity vector. This is the cutting angle that may be used in separating tissue layers, with the geometry for positive angles depicted in FIG. 79 and for negative angles depicted in FIG. 80.

As explained above at any given point in the cutting blade there are two velocity vectors. In the current design $\alpha=0$ as the blade is perpendicular to the cutting edge. Assume the cutting edge of the blade is divided into number of small elements (N). Each element is assumed to experience orthogonal cutting. The method of calculating dynamic rake angle at any instant and spatial position on the cutting edge can be developed based of geometric factors. Torque at each instant can be determined by the following equation:

$$T_{[total]} = \sum_{i=1}^{N} [F_p, F_n(f(\alpha_{d(i)}, woc(i)) \times r(i))]$$

Where $\alpha_d$ Dynamic Cutting Angle), and r(i) (radius of each element from the axis of the drill) is varying for each element on the cutting edge.

The difference between the current design and proposed design is that width of cutting edge (WOC) change, cutting angles may be steeper (range from 40 to 60 degrees) This is a converse problem of cutting as given 1 in-lb torque and X lbs thrust. What is the best geometry at the tip to get lower penetration force. This can be analytically developed and tested in the wet lab.

Problem statement is: $T_{total}$=constant–Reduce $F_n$ based of geometry.

This is possible with offset cutting edge and making more aggressive cutting angles from 40 to 60 degrees.

The cutting edge can also have multiple blades like 4 to increase the WOC. The cutting edge shall not be sharp to avoid ploughing. It may have a 5 thousand radius to optimize penetration forces. The flat blade can be further optimized as follows as depicted in FIGS. 81A-81B.

Figure 83:
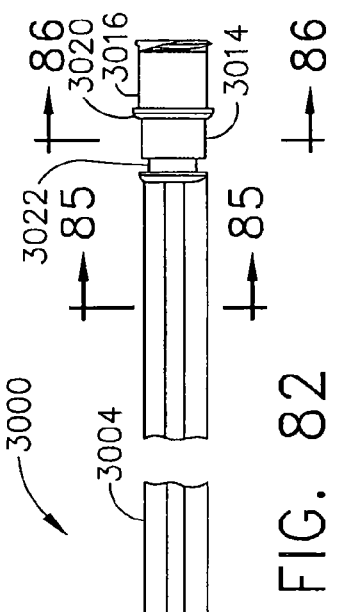
FIG. 83 is a front view in elevation of the obturator of FIG. 82.
Figure 82:
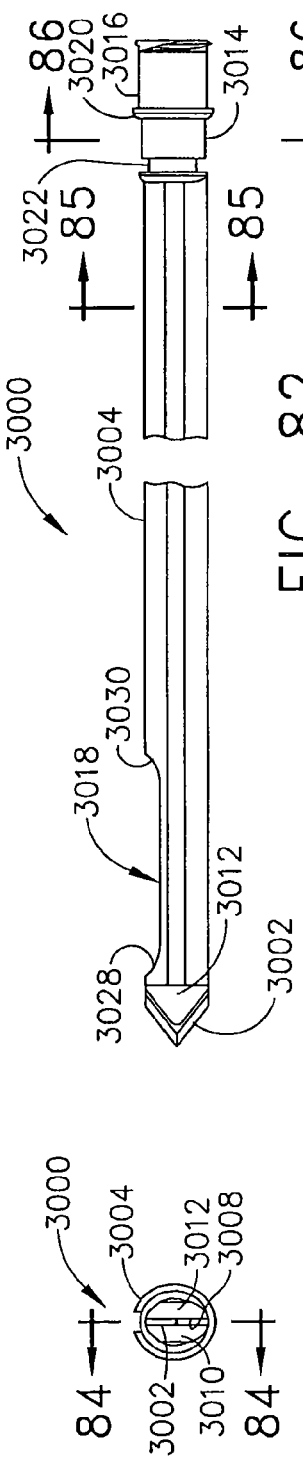
FIG. 82 is a left side view in elevation of an obturator with flat bladed piercing tip, lumen communicating between a lateral notch and fluid fitting on a proximal end with external engaging features for an obturator hub.
Figure 84:
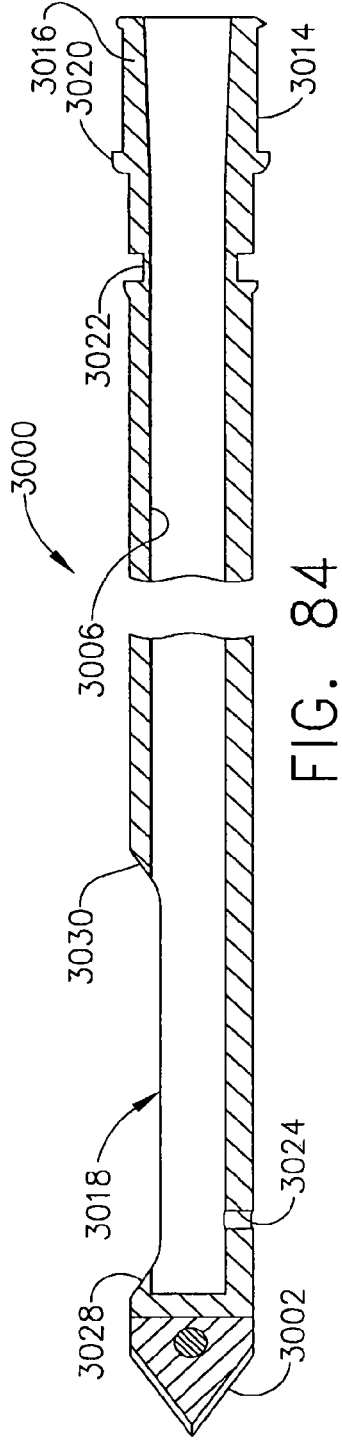
FIG. 84 is a left side view in elevation of a longitudinal cross section of the obturator of FIG. 83 taken along lines 84-84.
Figure 86:
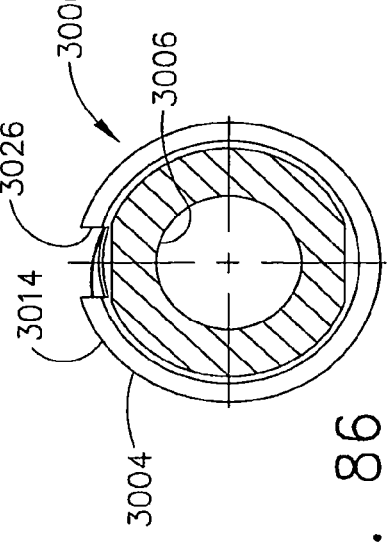
FIG. 86 is a front view in elevation of the obturator of FIG. 82 taken in cross section along lines 86-86 across the hub engaging portion.
Figure 85:
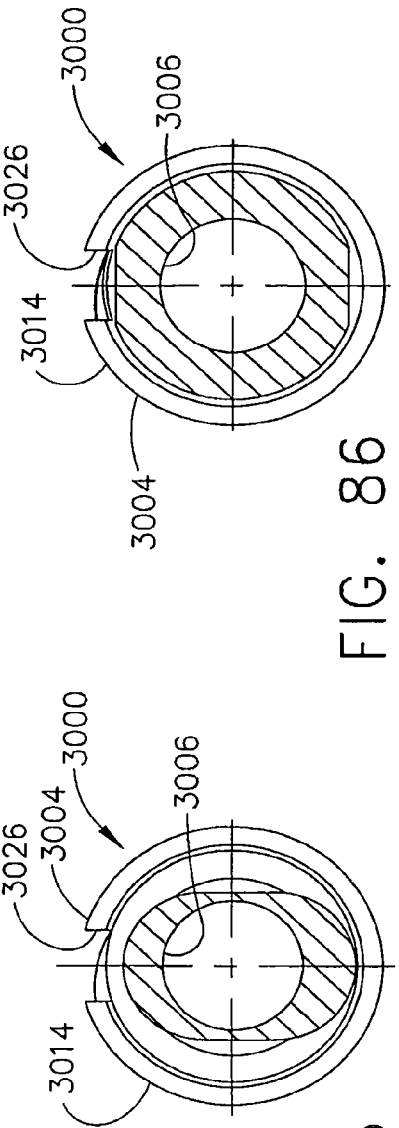
FIG. 85 is a front view in elevation of the obturator of FIG. 82 taken in cross section along lines 85-85 distal to a hub engaging portion.

In FIGS. 82-86, an obturator 3000 incorporates a flat blade 3002 onto a hollow shaft 3004 that provides a multi-function lumen 3006. In FIG. 83, the flat blade 3002 is attached within a vertical slot 3008 formed between two distal ramped triangular supports 3010, 3012. A proximal end 3014 of the hollow shaft 3004 provides a pressure fitting 3016 for using the lumen 3006 for pneumatic or fluid transfers to an imagable side notch 3018 proximate to the flat blade 3002. In FIGS. 82, 84, exterior engagement features on the proximal end 3014 include a circumferential raised ring 3020 proximal to a circumferential ring slot 3022. In FIG. 84, a vent hole 3024 through an opposite lateral side to the imagable side notch 3018 allows equalization of pressure within a sleeve or the use of a vacuum lumen in the sleeve (not shown in FIGS. 82-86). In FIGS. 85, 86, atop guide slot 3026 passes longitudinally down the proximal portion 3014 of the hollow shaft 3004 so that engagement with a sleeve may be keyed to align the imagable side notch 3018 with a side aperture in the sleeve. In FIGS. 82, 84, rounded leading and trailing edges 3028, 3030 of the imagable side notch 3018 minimize tissue trauma. Alternatively, the top guide slot 3026 may allow visual indexing so that confirmation may be made that the imagable side notch 3018 is rotated out of alignment with a side aperture during penetration to prevent tissue entering the image side notch 3018. Thereafter, the imagable side notch 3018 may be rotated into alignment for imaging confirmation and/or use of the multi-function lumen 3006.

It would be desirable to have disposable fiducial instruments that advantageously are fillable by the end user and may even be disposable. Thereby, clinical flexibility is enhanced by allowing the empty fiducial instrument to have extended shelf life, simplified sterilization processes, simplified storage (e.g., broader temperature range), and reduced packaging requirements. In addition, the end user may select a contrast agent or other imagable material.

Figure 87:
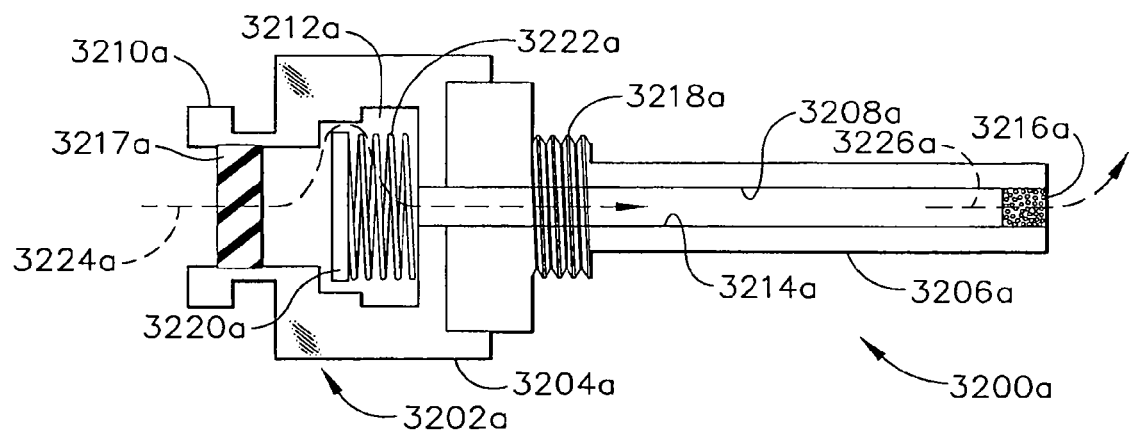
FIG. 87 is a right side view in elevation, taken in longitudinal cross section of the short fiducial instrument having a valve body attached to a hollow snout with a proximal fill spout sealed by a septum and proximally extending from the valve body and with the distal end of an elongate cavity in the hollow snout partially sealed by a porous plug.

In FIG. 87, a short fiducial instrument 3200a is an example of the fudicial 262 in FIG. 4 used with a localization fixture to locate a coordinate at an external point on the patient's skin. A clear polycarbonate body 3202a is assembled from a valve body 3204a attached to a hollow snout 3206a. An imaging lumen 3208a passes longitudinally from a proximal fill spout 3210a proximally extending from the valve body 3204a, through a one-way valve chamber 3212a into an elongate cavity 3214a in the hollow snout 3206a whose distal end is partially sealed by a porous plug 3216a. Examples of materials for the porous plug 3216a include porous PTFE, porous polyethylene, porous polypropylene, polystyrene, and glass frit. External threads 3218a on a proximal end of the hollow snout 3206a allow for engagement to a holder, such as a monocle or sleeve mount. In use, imagable fluid, such as but not limited to those materials described herein, are inserted into the proximal fill spout 3210a by inserting a syringe needle (not shown) through a septum 3217a that seals the proximal fill spout 3210a, causing a seal 3220a to unseat in the valve chamber 3212a compressing valve spring 3222a as the fluid enters the elongate chamber 3214a as depicted by arrow 3224a while air evacuates through porous plug 3216a as depicted by arrow 3226a. The end user continues to fill until evidently filled as viewed through a clear polycarbonate body 3202a, when resistance is felt to forcing in more fluid, or when the fill spout 3210a appears full, or when fluid begins to ooze through the porous plug 3216a. It should be appreciated that a two-way valve may be included that would allow an over-pressure to release fluid or for a user to withdraw fluid. In addition, the septum 3217a may suffice to hold fluid in the short fiducial instrument 3200a.

Figure 88:
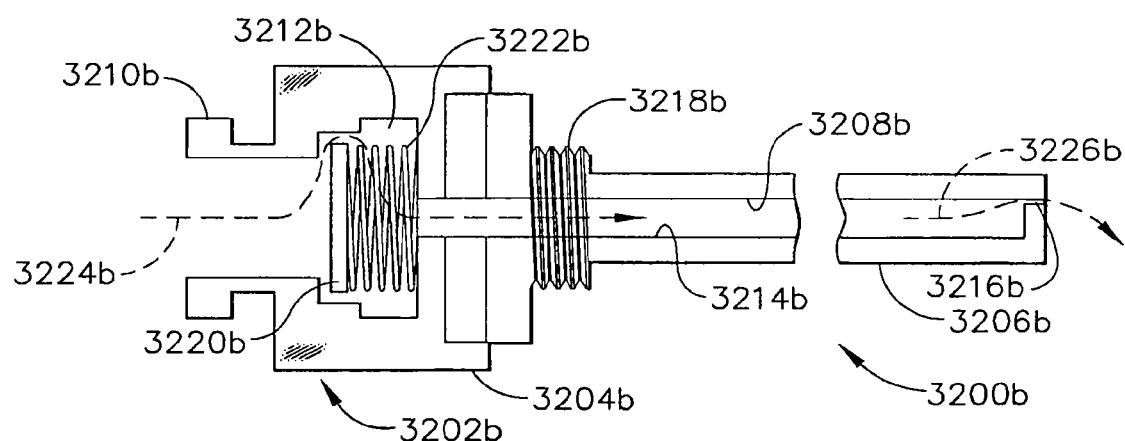
FIG. 88 is a right side view in elevation, taken in longitudinal cross section of the long fiducial instrument having an integral valve body portion formed with a hollow snout portion with a proximal pipe fitting proximally extending from the valve body portion and with the distal end of an elongate cavity in the hollow snout portion partially sealed by a vent hole.

In FIG. 88, a long fiducial instrument 3200b is an example of an imaging obturator or stylet or alternate features for a fiducial used external to the patient. Although not shown in FIG. 88 for clarity, a second open lumen may be included for inserting a tool. A piercing tip may also be included for use as an introducer obturator with an open ended sleeve. A clear polycarbonate body 3202b has an integral valve body portion 3204b formed with a hollow snout portion 3206b. An imaging lumen 3208b passes longitudinally from a proximal pipe fitting 3210b proximally extending from the valve body portion 3204b, through a one-way valve chamber 3212b into an elongate cavity 3214b in the hollow snout 3206b whose distal end is partially sealed by a small vent hole 3216b. External threads 3218b on a proximal end of the hollow snout 3206b allow for engagement to a holder, such as a sleeve hub. In use, imagable fluid, such as but not limited to those materials described herein, are inserted into the proximal pipe fitting 3210b, causing a seal 3220b to unseat in the valve chamber 3212b compressing closure valve spring 3222b as the fluid enters the elongate chamber 3214b as depicted by arrow 3224b while air evacuates through vent hole 3216b as depicted by arrow 3226b. After filling, surface tension of the liquid prevents loss of fluid through the vent hole 3216b.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, other imaging modalities may benefit from aspects of the present invention.

What is claimed is:

1. A method useful in imaging breast tissue, the method comprising the steps of:
   providing a sleeve having an internal lumen, an open distal end, and a tissue sample notch;
   providing an obturator having a distal bladed portion, wherein the obturator is removably insertable within the internal lumen of the sleeve to have the bladed portion extend from the open distal end of the sleeve and to have the sample notch of the sleeve closed by the obturator;
   inserting the obturator into the sleeve;
   inserting the sleeve and obturator into tissue to be sampled, with the obturator positioned to close the sample notch in the sleeve and with the bladed portion of the obturator extending from the open distal end of the sleeve; and
   at least partially opening the sample notch by moving the obturator relative to the sleeve;
   wherein the step of at least partially opening the sample notch is performed without withdrawing the distal bladed portion of the obturator from the open distal end of the sleeve.

2. The method of claim 1 further comprising the step of imaging the sample notch to determine the position of the sample notch with respect to a tissue mass, after at least partially opening the sample notch.

3. The method of claim 1 comprising the step of rotating the obturator within the internal lumen of the sleeve to at least partially open the sample notch.

4. The method of claim 1 comprising the step of retracting a portion of the obturator in a proximal direction to at least partially open the sample notch.

5. The method of claim 1 wherein the step of at least partially opening the sample notch comprises positioning a recess in the obturator with respect to the sample notch.

6. A method useful in imaging breast tissue, the method comprising the steps of:
- providing a sleeve having an internal lumen, an open distal end, and a tissue sample notch spaced proximally from the open distal end;
- providing an obturator, the obturator removably insertable within the internal lumen of the sleeve to have a distal portion of the obturator extend from the open distal end of the sleeve;
- inserting the obturator into the sleeve;
- inserting the sleeve and obturator into tissue to be sampled, with the obturator positioned in the sleeve to close the sample notch in the sleeve; and
- at least partially opening the sample notch by rotating the obturator relative to the sleeve.

7. A medical device for use in imaging breast tissue; the apparatus comprising:
- a sleeve having an internal lumen sized to receive a biopsy device, an open distal end;
- and a sample notch disposed proximally of the open distal end;
- an obturator having a bladed distal end, the obturator removably insertable within the sleeve, wherein the obturator is movable within the sleeve from a first configuration to a second configuration;
- wherein in the first configuration the bladed distal end extends from the open distal end of the sleeve and the obturator substantially closes the sample notch in the sleeve; and
- wherein in the second configuration the bladed distal end extends from the open distal end of the sleeve and a portion of the obturator is positioned to substantially open the sample notch in the sleeve.

8. The device of claim 7 wherein the obturator comprises a recess, and wherein the recess in the obturator is spaced circumferentially from the sample notch in the first configuration, and wherein the recess in the obturator is generally aligned with the sample notch in the second configuration.

9. The device of claim 7 wherein the obturator is rotatable within sleeve from the first configuration to the second configuration.

10. The device of claim 7 wherein a portion of the obturator adjacent the sample notch in the first configuration is displaced proximally of the sample notch in the second configuration.

* * * * *